United States Patent
Ozcan et al.

(10) Patent No.: US 12,064,408 B2
(45) Date of Patent: *Aug. 20, 2024

(54) COMPOUNDS FOR THE TREATMENT OF OBESITY AND METHODS OF USE THEREOF

(71) Applicants: The Children's Medical Center Corporation, Boston, MA (US); The General Hospital Corporation, Boston, MA (US)

(72) Inventors: Umut Ozcan, Boston, MA (US); Joseph Majzoub, Boston, MA (US); Ralph Mazitschek, Belmont, MA (US)

(73) Assignees: The Children's Medical Center Corporation, Boston, MA (US); The General Hospital Corporation, Boston, MA (US)

(*) Notice: Subject to any disclaimer, the term of this patent is extended or adjusted under 35 U.S.C. 154(b) by 110 days.

This patent is subject to a terminal disclaimer.

(21) Appl. No.: 17/326,944

(22) Filed: May 21, 2021

(65) Prior Publication Data

US 2021/0275482 A1    Sep. 9, 2021

Related U.S. Application Data

(63) Continuation of application No. 16/860,232, filed on Apr. 28, 2020, now Pat. No. 11,045,439, which is a continuation of application No. 15/908,571, filed on Feb. 28, 2018, now Pat. No. 10,653,654, which is a continuation of application No. 14/431,412, filed as application No. PCT/US2013/061911 on Sep. 26, 2013, now Pat. No. 9,968,575.

(60) Provisional application No. 61/706,153, filed on Sep. 27, 2012.

(51) Int. Cl.
| | |
|---|---|
| *A61K 31/198* | (2006.01) |
| *A61K 31/19* | (2006.01) |
| *A61K 31/192* | (2006.01) |
| *A61K 31/194* | (2006.01) |
| *A61K 31/195* | (2006.01) |
| *A61K 38/22* | (2006.01) |
| *A61K 45/06* | (2006.01) |
| *A61P 3/04* | (2006.01) |

(52) U.S. Cl.
CPC ............ *A61K 31/198* (2013.01); *A61K 31/19* (2013.01); *A61K 31/192* (2013.01); *A61K 31/194* (2013.01); *A61K 31/195* (2013.01); *A61K 38/2264* (2013.01); *A61K 45/06* (2013.01); *A61P 3/04* (2018.01)

(58) Field of Classification Search
None
See application file for complete search history.

(56) References Cited

U.S. PATENT DOCUMENTS

| | | |
|---|---|---|
| 5,650,167 A | 7/1997 | Allison |
| 8,236,769 B2 | 8/2012 | Tanaka |
| 8,299,125 B2 | 10/2012 | Zeng |
| 9,968,575 B2 | 5/2018 | Ozcan |
| 2007/0111994 A1 | 5/2007 | Glick |
| 2007/0160692 A1 | 7/2007 | Tripp |
| 2008/0044390 A1 | 2/2008 | Jin |
| 2009/0054438 A1 | 2/2009 | Ronai |
| 2009/0203605 A1 | 8/2009 | Segatori |
| 2010/0240581 A1 | 9/2010 | Tortoriello |
| 2011/0281955 A1 | 11/2011 | Meyer |
| 2012/0041228 A1 | 2/2012 | Hosoi |
| 2012/0052019 A1 | 3/2012 | Qian |

FOREIGN PATENT DOCUMENTS

| | | |
|---|---|---|
| CN | 101805390 | 8/2010 |
| CN | 103524592 | 1/2014 |
| EP | 2213679 | 8/2010 |
| RU | 2346688 | 2/2009 |
| WO | 2007117466 | 10/2007 |
| WO | 2009026163 | 12/2008 |
| WO | 2009067245 | 5/2009 |
| WO | 2009100037 | 8/2009 |
| WO | 2012024893 | 3/2012 |
| WO | 2013177535 | 2/2013 |
| WO | 2014052583 | 1/2014 |

OTHER PUBLICATIONS

Brakenheilm, et al., "Angiogenesis inhibitor, TNP-470, prevents diet-induced and genetic obesity in mice", Circ Res., 94(12):1579-88 (2011).

(Continued)

*Primary Examiner* — Sudhakar Katakam
*Assistant Examiner* — Jennifer C Sawyer
(74) *Attorney, Agent, or Firm* — PABST PATENT GROUP LLP

(57) ABSTRACT

Pentacyclic triterpene weight loss agents are provided herein. Also provided are pharmaceutical formulations containing a therapeutically effective amount of one or more of the weight loss agents, or pharmaceutically acceptable salts or prodrugs thereof, in combination with one or more pharmaceutically acceptable excipients. The pharmaceutical formulations can be administered to a pre-obese, obese, or morbidly obese patient to induce weight loss, reduce body fat, reduce food intake, improve glucose homeostasis, prevent obesity, or a combination thereof. The weight loss agents can also be co-administered with leptin or a leptin analog.

19 Claims, 24 Drawing Sheets

(56) References Cited

OTHER PUBLICATIONS

Cao, "Angiogenesis modulates adipogenesis and obesity", J. Clin. Invest., 117(9):2362-8 (2007).

Corson, et al., "Molecular understanding and modern application of traditional medicines: triumphs and trials", Cell, 130(5):769-74 (2007).

De Melo, et al., "Oleanolic acid, a natural triterpenoid improves blood glucose tolerance in normal mice and ameliorates visceral obesity in mice fed a high-fat diet", Chem Biol Interact, 185(1):59-65 (2010).

Dhanesha, et al., "Inhibition of 11β-hydroxysteroid dehydrogenase 1 by carbenoxolone affects glucose homeostasis and obesity in db/db mice", Clin Exp Pharmacol Physiol., 39(1):69-77 (2012).

Ejaz, et al., "Curcumin inhibits adipogenesis in 3T3-L1 adipocytes and angiogenesis and obesity in C57/BL mice", J Nutr, 139(5):919-25 (2008).

Friedman, "Leptin and the regulation of body weight", https://www.jstage.jsi.go.jp/article/kjm/60/1/60_1_1,pp. 1-9 Dec. 27, 2011, retrieved from the internet Jun. 30, 2016.

Gupta and Rana, "PHCOG Mag: Plant review withania somnifera (ashwagandha): A review", PHCOG Rev., 1:129-36 (2007).

Ichinose, et al., "2-(8-hydroxy-6-methoxy-1-oxo-1h-2-benzopyran-3-yl) propionic acid, an inhibitor of angiogenesis, ameliorates renal alterations in obese type 2 diabetic mice", Diabetes, 55:1232-42 (2006).

International Search Report for PCT/US2013/061911 mailed Jan. 3, 2014.

Jeong, et al., "Antiangiogenic Pytochemicals and medicinal Herbs", Phyto Res., 25:1-10 (2011).

Johnson, et al., "536, Pristimerin, part IV, total structure", J Chem Society,pp. 2884-2889 (1963).

Kaileh, et al., Withaferin a Strong elicit Withaferin a strongly elicits IkappaB kinase beta hyperphosphorylation concomitant with potent inhibition of its kinase activity , J Biol Chem., 282(7):4253-64 (2007).

Klaic, et al.., "Remarkable stereospecific conjugate additions to the Hsp90 inhibitor celastrol", J Chem Society, 133(49):19634-7 (2011).

Kusakabe, et al., "Congenital deficiency of leptin and its receptor in humans", Nippon Ronsho, 68, Extra Edition 2, (2010).

Kutney, et al., "Cytotoxic diterpenes triptolide, tripdiolide, and cytotoxic triterpenes from tissue cultures of Tripterygium wilfordii", Can J Chem., 59(17):2677-83 (1981).

Lee, et al., The Effect of Celastrol on Metabllic Distrubances and Renal Injury in High Fat Diet-induced Obesity Mice, Korean J Nephrology, S423 (2011).

Lijnen, "Angiogenesis and obesity", Caradiovasc Res, 78(2):286-93 (2008).

Liu, et al., "Treatment of obesity with celaztrol", Cell, 161(5):999-1011 (2015).

Madupu, et al, "Aswagandha (withania somnifera)-ayurvedic bequest for the patients of cancer: An update on current research", IJRAP, 1(2):234-8 (2010).

Mishra, et al., "Scientific basis for the therapeutic use of withania somnifera (ashwagandha): A review", Alternative Med Rev., 5(4):334-46 (2000).

Mu, et al., Chemical and biological approaches synergize to ameliorate protein folding diseases, Cell, 134:769-81 (2008).

Ozcan, et al., "Endoplasmic reticulum stress plays a central role in development of leptin resistance", Cell metabolism, 9:35-51 (2009).

Singh, et al., "Biological activities of Withania somnifera", Annals Biologic Res., 1(3):56-63 (2010).

South, "Stress and cortisol: the plague of the 21st centrury", http://www.worldwidehealthcenter.net, accessed May 2, 2011.

Sreeramulu, et al., "Molecular Mechanism of Inhibition of the Human Protein Complex Hsp90-Cdc37, a Kinome Chpaerone-Cochaperone, by Triterpene Celastrol", Agnew. Chem. Int. Ed. 48:5853 (2009).

Sreeramulu, et al., "Molecular Mechanism of Inhibition of the Human Protein Complex Hsp90-Cdc37, a Kinome Chpaerone-Cochaperone, by Triterpene Celastrol", Agnew. Chem. Int. Ed. 48:5853 (2009). Supporting Information.

Sun, et al., "Synthesis and preliminary evaluation of neuorprotection of celastrol analogues in PC12 cells", Bioorganic Medicanl Chem. Ltrs., 20:3844-3847 (2010).

Voros, et al., "Modulation of angiogenesis during adipose tissue development in murine models of obesity", Endocrinology, 146(10):4545-54 (2005).

Wang, et al., "Celastrol suppresses obesity process via increasing antioxidant capacity and improving lipid metabolism", Eu J Pharmacology, 744:52-8 (2014).

Westerheide, et al., "Celastrols as inducers of the heat shock response and cytoprotection", J Biol Chem, 279(53):56053-60 (2004).

Yang, et al., "Celastrol, a triterpene extracted from the Chinese "Thunder of God Vine," is a potent proteasome inhibitor and suppresses human prostate cancer growth in nude mice", Cancer Res., 66:4758-65 (2006).

Yang, et al., "The tumor proteasome is a primary target for the natural anticancer compound withaferin A isolated from Indian winter cherry", Molecular Pharmacology, 71(2):426-37 (2007).

Yokota, et al., "Development of withaferin A analogs as probes of angiogenesis", Bioorg Medicinal Chem Lttrs., 16(10:2603-7 (2006).

COMPOUNDS FOR THE TREATMENT OF OBESITY AND METHODS OF USE THEREOF

CROSS-REFERENCE TO RELATED APPLICATIONS

This application is a continuation of U.S. application Ser. No. 16/860,232 filed Apr. 28, 2020, which is a continuation of U.S. application Ser. No. 15/908,571 filed Feb. 28, 2018, now U.S. Pat. No. 10,653,654 issued May 19, 2020, which is a continuation of U.S. application Ser. No. 14/431,412, filed Mar. 26, 2015, now U.S. Pat. No. 9,968,575, issued May 15, 2018, which is a National Phase application under 35 U.S.C. § 371 of International Application No. PCT/US2013/061911, filed Sep. 26, 2013, which claims the benefit of and priority to U.S. Provisional Application No. 61/706,153, filed Sep. 27, 2012, and are hereby incorporated herein by reference in their entirety.

FIELD OF THE INVENTION

This invention is in the field of compounds to regulate obesity, and methods of making and using thereof.

BACKGROUND OF THE INVENTION

Obesity is a medical condition in which excess body fat has accumulated to the extent that it may have an adverse effect on health, leading to reduced life expectancy and/or increased health problems. Body mass index (BMI), a measurement which compares weight and height, defines people as overweight (pre-obese or overweight) if their BMI is between 25 and 30 kg/m$^2$, and obese when it is greater than 30 kg/m$^2$. Obesity is a leading preventable cause of death worldwide, with increasing prevalence in adults and children, and authorities view it as one of the most serious public health problems of the 21st century.

Obesity increases the risk of many physical and mental disorders. Excessive body weight is associated with various diseases, particularly cardiovascular diseases, diabetes mellitus type 2, obstructive sleep apnea, certain types of cancer, and osteoarthritis. These diseases are either directly caused by obesity or indirectly related through mechanisms sharing a common cause such as a poor diet and/or a sedentary lifestyle. One of the strongest links is with type 2 diabetes. Excess body fat underlies 64% of cases of diabetes in men and 77% of cases in women. Increases in body fat alter the body's response to insulin, potentially leading to insulin resistance.

Obesity is most commonly caused by a combination of excessive energy intake, lack of physical activity, and genetic susceptibility, although a few cases are caused primarily by genes, endocrine disorders, medications or psychiatric illness. Since the discovery of leptin in 1994, many other hormonal mechanisms have been elucidated that participate in the regulation of appetite and food intake, storage patterns of adipose tissue, and development of insulin resistance, including ghrelin, insulin, orexin, PYY 3-36, cholecystokinin, and adiponectin.

Adipokines are mediators produced by adipose tissue; their action is thought to modify many obesity-related diseases. Leptin and ghrelin are considered to be complementary in their influence on appetite, with ghrelin produced by the stomach modulating short-term appetitive control (i.e., to eat when the stomach is empty and to stop when the stomach is stretched). Leptin is produced by adipose tissue to signal fat storage reserves in the body, and mediates long-term appetitive controls (i.e., to eat more when fat storages are low and less when fat storages are high). Although administration of leptin may be effective in a small subset of obese individuals who are leptin deficient, most obese individuals are thought to be leptin resistant and have been found to have high levels of leptin. This resistance is thought to explain in part why administration of leptin has not been shown to be effective in suppressing appetite in most obese people.

While leptin and ghrelin are produced peripherally, they control appetite through their actions on the central nervous system. In particular, leptin and ghrelin and other appetite-related hormones act on the hypothalamus, a region of the brain central to the regulation of food intake and energy expenditure. There are several circuits within the hypothalamus that contribute to its role in integrating appetite, with the melanocortin pathway being the most-well understood. The circuit begins with the arcuate nucleus, an area of the hypothalamus that has outputs to the lateral hypothalamus and ventromedial hypothalamus, the brain's feeding and satiety centers, respectively.

The arcuate nucleus contains two distinct groups of neurons. The first group co-expresses neuropeptide Y (NPY) and agouti-related peptide (AgRP) and has stimulatory inputs to the LH and inhibitory inputs to the VMH. The second group co-expresses pro-opiomelanocortin (POMC) and cocaine- and amphetamine-regulated transcript (CART) and has stimulatory inputs to the VMH and inhibitory inputs to the LH. Consequently, NPY/AgRP neurons stimulate feeding and inhibit satiety, while POMC/CART neurons stimulate satiety and inhibit feeding. Both groups of arcuate nucleus neurons are regulated in part by leptin. Leptin inhibits the NPY/AgRP group while stimulating the POMC/CART group. Thus a deficiency in leptin signaling, either via leptin deficiency or leptin resistance, leads to overfeeding. This may account for some genetic and acquired forms of obesity.

Dieting and physical exercise are the mainstays of treatment for obesity. To supplement these activities, or in case of failure, anti-obesity drugs may be taken to reduce appetite or inhibit fat absorption. In severe cases, surgery is performed or an intragastric balloon is placed to reduce stomach volume and/or bowel length, leading to earlier satiation and reduced ability to absorb nutrients from food. Maintaining this weight loss is frequently difficult and often requires making exercise and a lower food energy diet a permanent part of a person's lifestyle. Success rates of long-term weight loss maintenance with lifestyle changes are low, ranging from 2-20%.

A limited number of medications are available for the treatment of obesity. Concerns about side effects have diminished enthusiasm for appetite-suppressant drugs, particularly fenfluramine, sibutramine, and phentermine, which carry serious risks and have been withdrawn from the market. Phentermine is approved only for short-term use. Orlistat (Xenical) is a medication that blocks the absorption of dietary fat and is also approved for longer-term use. However, it causes unpleasant side effects (greasy stool), and requires supplementation with fat-soluble vitamins.

Although surgery (such as gastric bypass) is the last resort for the treatment of obesity, it can be extremely effective. However, it should be performed at an experienced surgical center, because such operations can carry significant risks, especially in the post-operative period. Consensus recommendations are to limit surgical therapies to patients with morbid obesity (BMI>40, BMI>35 plus co-morbidities, or BMI>30 with uncontrollable diabetes).

A number of weight-loss pills are available at local drugstores, supermarkets or health food stores. Even more options are available online. Most have not been proved effective, and some may be dangerous. Table 1 (below) shows common weight-loss pills and what the research shows about their effectiveness and safety.

Herbal extracts are often impure and contain so many different substances, that it is difficult to assess if the mixture as a whole is efficacious, much less what constitutes an effective dosage. With hundreds or more different compounds in the mixture, it could be more than one compound required for activity, or one compound inhibiting activity of another compound, so the source and processing of the original source material may result in an inactive or even dangerous product.

TABLE 1

Anecdotal Products for Weight Loss. Sources: U.S. Food and Drug Administration, 2010; Natural Medicines Comprehensive Database, 2010

| Product | Claim | Effectiveness | Safety |
| --- | --- | --- | --- |
| Alli-OTC version of prescription drug orlistat (Xenical) | Decreases absorption of dietary fat | Effective; weight-loss amounts typically less for OTC versus prescription | FDA investigating reports of liver injury |
| Bitter orange | Increases calories burned | Insufficient reliable evidence to rate | Possibly unsafe |
| Chitosan | Blocks absorption of dietary fat | Insufficient reliable evidence to rate | Possibly safe |
| Chromium | Increases calories burned, decreases appetite and builds muscle | Insufficient reliable evidence to rate | Likely safe |
| Conjugated linoleic acid (CLA) | Reduces body fat and builds muscle | Possibly effective | Possibly safe |
| Country mallow (heartleaf) | Decreases appetite and increases calories burned | Insufficient reliable evidence to rate | Likely unsafe and banned by FDA |
| Ephedra | Decreases appetite | Possibly effective | Likely unsafe and banned by FDA |
| Green tea extract | Increases calorie and fat metabolism and decreases appetite | Insufficient reliable evidence to rate | Possibly safe |
| Guar gum | Blocks absorption of dietary fat and increases feeling of fullness | Possibly ineffective | Likely safe |
| Hoodia | Decreases appetite | Insufficient reliable evidence to rate | Insufficient information |

It is therefore an object of the present invention to provide safe, well characterized and efficacious compounds for effecting weight loss, and methods of use thereof.

It is a further object of the present invention to provide dosage forms, such as oral dosage forms, for the promotion of weight loss, and methods of use thereof.

SUMMARY OF THE INVENTION

Active agents for the promotion of weight loss, as well as formulations containing these active agents and methods of using thereof, are described herein.

Exemplary weight loss agents include compounds defined by Formula I

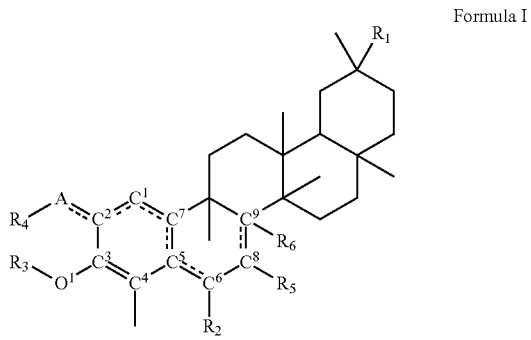

Formula I wherein
the dotted lines between A and $C^2$, $C^1$ and $C^2$, $C^1$ and $C^7$, $C^7$ and $C^5$, $C^5$ and $C^6$, and $C^8$ and $C^9$ indicate that a single or double bond may be present, as valence permits;

$R_1$ is a carboxylic acid (—COOH), primary amide (e.g., —$CONH_2$), secondary amide (e.g., —$CONHR_7$), tertiary amide (e.g., —$CONR_7R_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —NR—$CONHR_7$; —$NHCONR_7R_7$, —$NR_7CONR_7R_7$), carbinol (e.g., —$CH_2OH$; —$CHR_7OH$, —$CR_7R_7OH$), ether (e.g., —$OR_7$), ester (e.g., —$COOR_7$), alcohol (—OH), thiol (—SH), primary amine (—$NH_2$), secondary amine (e.g., —$NHR_7$), tertiary amine (e.g., —$NR_7R_7$), thioether (e.g., —$SR_7$), sulfinyl group (e.g., —$SOR_7$), sulfonyl group (e.g., —$SOOR_7$), sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_2$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —$NR_7COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

A is nitrogen or oxygen when a double bond is present between A and $C^2$, or oxygen or NR when a single bond is present between A and $C^2$, wherein R is defined the same $R_1$;

$R_3$ is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_4$ is absent when A is oxygen and a double bond is present between A and $C^2$, a hydroxy (—OH) group when A is nitrogen and a double bond is present between A and $C^2$, or is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when A is oxygen or NR and a single bond is present between A and $C^2$; or A is oxygen or NR, a single bond is present between A and $C^2$, and $R_3$ and $R_4$, taken together with A, $C^2$, $C^3$, and $O^1$, form a 5- to 7-membered ring optionally substituted with between one and four substituents individually selected from alkyl, cyclopropyl, cyclobutyl ether, amine, halogen, hydroxyl, ether, nitrile, $CF_3$, ester, amide, urea, carbamate, thioether, and carboxylic acid;

$R_5$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_6$ is absent when a double bond is present between $C^8$ and $C^9$, is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —NR—$COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when a single bond is present between $C^8$ and $C^9$; or a single bond is present between $C^8$ and $C^9$, and $R_5$ and $R_6$, taken together with $C_8$ and $C_9$, form a cyclopropyl or epoxide ring; and $R_7$, when present, is individually for each occurrence an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

or a pharmaceutically acceptable salt or prodrug thereof.

In some embodiments of Formula I, a double bond is present between A and $C^2$, $C^1$ and $C^7$, $C^5$ and $C^6$, and $C^8$ and $C^9$, and a single bond is present between $C^1$ and $C^2$, and $C^7$ and $C^5$. In other embodiments of Formula I, a double bond is present between $C^1$ and $C^2$, $C^7$ and $C^5$, and $C^8$ and $C^9$, and a single bond is present between A and $C^2$, $C^1$ and $C^7$, and $C^5$ and $C^6$.

In particular embodiments of Formula I, $R_1$ is a carboxylic acid, ester, or amide; $R_2$ is hydrogen, an ether (—$OR_7$) or thioether (—$SR_7$); and Ry is a $C^1$-$C^{12}$, more preferably $C^1$-$C^8$ alkyl group optionally substituted with between one and three substituents individually selected from alkyl, amine, halogen, hydroxyl, ester, amide, and carboxylic acid.

In certain embodiments, the weight loss agent is a compound defined by Formula II

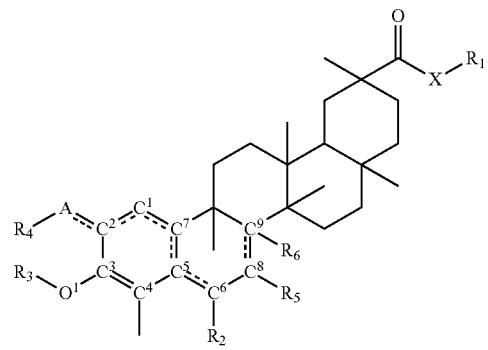

Formula II wherein
the dotted lines between A and $C^2$, $C^1$ and $C^2$, $C^1$ and $C^7$, $C^7$ and $C^5$, $C^5$ and $C^6$, and $C^8$ and $C^9$ indicate that a single or double bond may be present, as valence permits;

X is —O—, —$NR_7$—, —S—, —SO—, or —$SO_2$—;

$R_1$ is hydrogen, or an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, and aryl;

$R_2$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —NR—$COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

A is nitrogen or oxygen when a double bond is present between A and $C^2$, or oxygen or NR when a single bond is present between A and $C^2$;

$R_3$ is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_4$ is absent when A is oxygen and a double bond is present between A and $C^2$, a hydroxy (—OH) group when A is nitrogen and a double bond is present between A and $C^2$, or is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when A is oxygen or NR and a single bond is present between A and $C^2$; or A is oxygen or nitrogen, a single bond is present between A and $C^2$, and $R_3$ and $R_4$, taken together with A, $C^2$, $C^3$, and $O^1$, form a 5- to 7-membered ring optionally substituted with between one and four substituents individually selected from alkyl, cyclopropyl, cyclobutyl ether, amine, halogen, hydroxyl, ether, nitrile, $CF_3$, ester, amide, urea, carbamate, thioether, and carboxylic acid;

$R_5$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_6$ is absent when a double bond is present between $C^8$ and $C^9$, is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when a single bond is present between $C^8$ and $C^9$; or a single bond is present between $C^8$ and $C^9$, and $R_5$ and $R_6$, taken together with $C_8$ and $C^9$, form a cyclopropyl or epoxide ring; and $R_7$, when present, is individually for each occurrence an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

or a pharmaceutically acceptable salt or prodrug thereof.

In some embodiments of Formula II, a double bond is present between A and $C^2$, $C^1$ and $C^7$, $C^1$ and $C^6$, and $C^8$ and $C^9$, and a single bond is present between $C^1$ and $C^2$, and $C^7$ and $C^5$. In other embodiments of Formula II, a double bond is present between $C^1$ and $C^2$, $C^7$ and $C^5$, and $C^8$ and $C^9$, and a single bond is present between A and $C^2$, $C^1$ and $C^7$, and $C^5$ and $C^6$.

In some embodiments of Formula II, X is O or —$NR_7$—; $R_1$ is hydrogen or alkyl group optionally substituted with between one and three substituents individually selected from alkyl, amine, halogen, hydroxyl, ester, amide, and carboxylic acid; $R_2$ is hydrogen, an ether (—$OR_7$) or thioether (—$SR_7$); and $R_7$ is, individually for each occurrence, a $C^1$-$C^{12}$, more preferably $C^1$-$C^8$ alkyl group optionally substituted with between one and three substituents individually selected from alkyl, amine, halogen, hydroxyl, ester, amide, and carboxylic acid.

The compounds described above can have one or more chiral centers and therefore can exist as two or more unique stereoisomers. In some embodiments, the compounds described herein have the following stereochemistry:

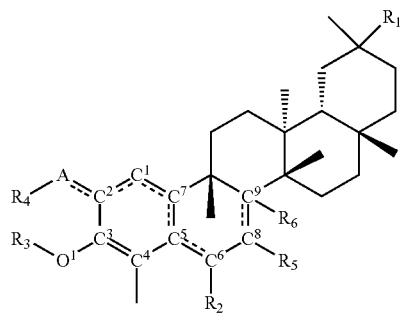

or

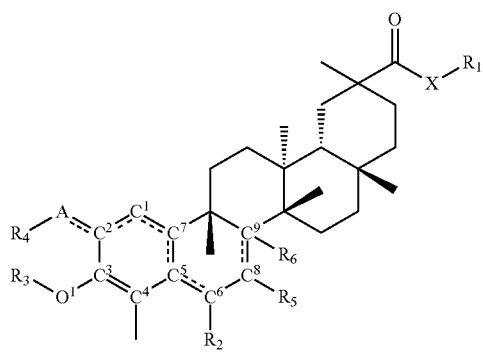

In particular embodiments, the weight loss agent is one of the following

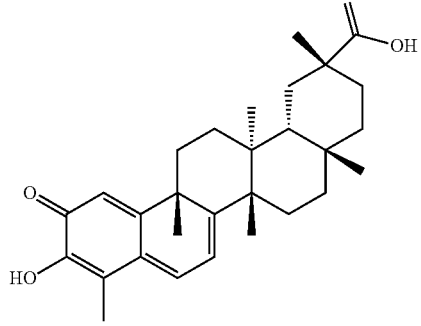

Celastrol

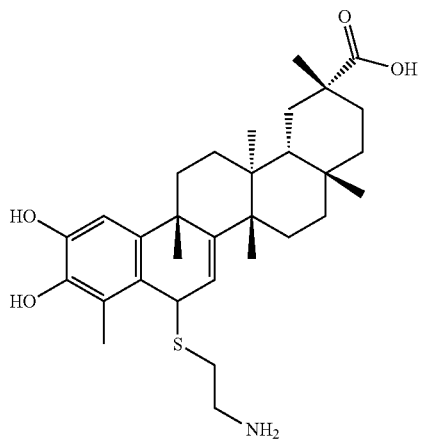

mCS1

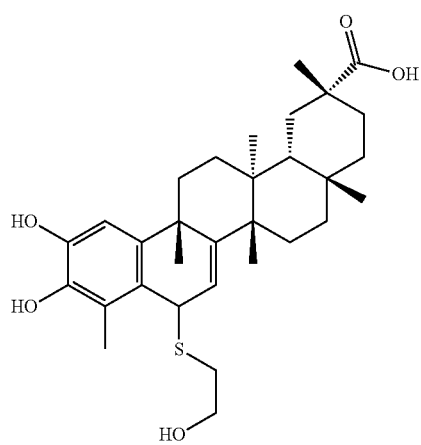

mCS2

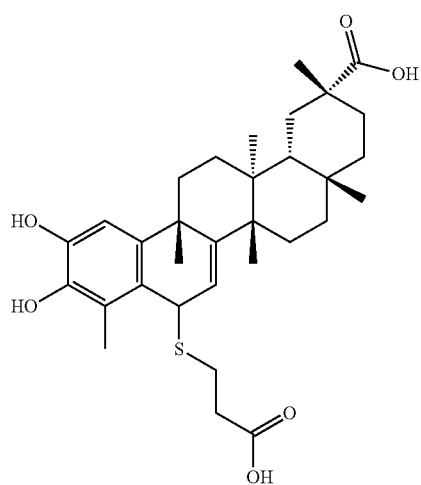

mCS3

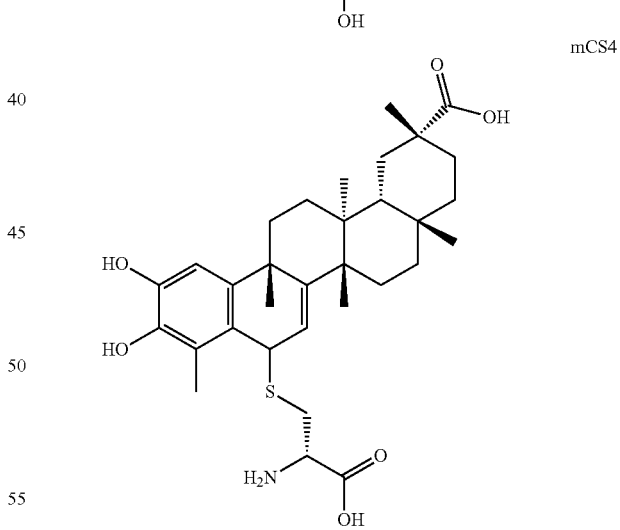

mCS4

Also provided are pharmaceutical formulations containing a therapeutically effective amount of a weight loss agent, or a pharmaceutically acceptable salt or prodrug thereof, in combination with one or more pharmaceutically acceptable excipients. The pharmaceutical formulations can be administered to induce weight loss in a pre-obese, obese, or morbidly obese patient, reduce body fat in a pre-obese, obese, or morbidly obese patient, reduce food intake in a pre-obese, obese, or morbidly obese patient, improve glucose homeostasis in a pre-obese, obese, or morbidly obese patient, or combinations thereof.

In particular embodiments, the weight loss agent is co-administered with leptin or a leptin analog, such as r-metHu-Leptin (A-100, METRELEPTIN®), available from Amylin Pharmaceuticals (San Diego, Calif.).

In some cases, a pharmaceutical formulation containing one or more of the weight loss agents is administered to a pre-obese, obese, or morbidly obese patient in a therapeutically effective amount to induce weight loss, preferably in a therapeutically effective amount and time of administration to decrease body mass or body fat by at least 10%, more preferably by at least 15%, most preferably by at least 20%, or higher.

In some cases, a pharmaceutical formulation containing one or more of the weight loss agents is administered to a pre-obese, obese, or morbidly obese patient in a therapeutically effective amount to reduce food intake, appetite, or combinations thereof, preferably in a therapeutically effective amount to reduce average daily food intake (in terms of calories) by at least 15%, 17%, 20%, 22%, 25%, 28%, 30%, 32%, 35%, or higher.

In some cases, a pharmaceutical formulation containing one or more of the weight loss agents is administered to a pre-obese, obese, or morbidly obese patient in a therapeutically effective amount to improve glucose homeostasis, preferably in a therapeutically effective amount to reduce average fasting plasma blood glucose by at least 10%, 12%, 15%, 18%, 20%, 22%, 25%, or higher. In cases where the pharmaceutical formulations are administered to normalize blood sugar, the formulations are preferably administered in an amount effective to lower blood glucose levels to less than about 180 mg/dL. The formulations can be co-administered with other anti-diabetic therapies, if necessary, to improve glucose homeostasis.

BRIEF DESCRIPTION OF THE DRAWINGS

FIG. 1A is a graph plotting the bodyweight of HFD-fed obese mice (in grams) as a function of time (days) for treatment with celastrol at different doses (vehicle control (diamond trace), 10 μg/kg celastrol by i.p. once a day (circle trace), 50 μg/kg celastrol by i.p. once a day (triangle trace), and 100 μg/kg celastrol by i.p. once a day (square trace)). FIG. 1B is a graph plotting the percent decrease in the bodyweight of HFD-fed obese mice (in grams) as a function of time (days) for treatment with celastrol at different doses (vehicle control (diamond trace), 10 μg/kg celastrol by i.p. once a day (circle trace), 50 μg/kg celastrol by i.p. once a day (triangle trace), and 100 μg/kg celastrol by i.p. once a day (square trace)). FIG. 1C is a bar graph illustrating the food intake (in grams/day) of HFD-fed obese mice during the course of treatment with celastrol at different doses (from left to right, vehicle control, 10 μg/kg celastrol by i.p. once a day, 50 μg/kg celastrol by i.p. once a day, and 100 μg/kg celastrol by i.p. once a day). FIG. 1D is a bar graph illustrating the 6 hour fasting blood glucose level (in mg/dL) of HFD-fed obese mice at the end of two weeks of treatment with celastrol at different doses (from left to right, vehicle control, 10 μg/kg celastrol by i.p. once a day, 50 μg/kg celastrol by i.p. once a day, and 100 μg/kg celastrol by i.p. once a day). In all cases, n=5 mice per group. *, $p<0.05$;, $p<0.01$;*, $p<0.001$ by Student's t-test. The results are based on the daily food intake data taken during the first three days.

FIG. 2A is a graph plotting the bodyweight of lean mice (in grams) as a function of time (days) for treatment with celastrol at different doses (vehicle control (diamond trace), 50 μg/kg celastrol by i.p. once a day (circle trace), 100 μg/kg celastrol by i.p. once a day (triangle trace), and 500 μg/kg celastrol by i.p. once a day (square trace)). FIG. 2B is a bar graph illustrating the food intake (in grams/day) of lean mice during the course of treatment with celastrol at different doses (from left to right, vehicle control, 50 μg/kg celastrol by i.p. once a day, 100 μg/kg celastrol by i.p. once a day, and 500 μg/kg celastrol by i.p. once a day). FIG. 2C is a bar graph illustrating the 6 hour fasting blood glucose level (in mg/dL) of lean mice at the end of two weeks of treatment with celastrol at different doses (from left to right, vehicle control, 10 μg/kg celastrol by i.p. once a day, 50 μg/kg celastrol by i.p. once a day, and 100 μg/kg celastrol by i.p. once a day). In all cases, n=5 mice per group. *, $p<0.05$;, $p<0.01$;*, $p<0.001$ by Student's t-test.

FIG. 3A is a graph plotting the bodyweight of ob/ob mice (in grams) as a function of time (days) for treatment with celastrol (vehicle control (diamond trace), 100 μg/kg celastrol in 25 μL DMSO by i.p. once a day (square trace)). FIG. 3B is a bar graph illustrating the food intake (in grams/day) of ob/ob mice during the course of treatment with celastrol (left bar, vehicle control; right bar, 100 μg/kg celastrol by i.p. once a day). FIG. 3C is a bar graph illustrating the 6 hour fasting blood glucose level (in mg/dL) of ob/ob mice at the end of two weeks of treatment with celastrol (left bar, vehicle control; right bar, 100 μg/kg celastrol by i.p. once a day). In all cases, n=5 mice per group. *, $p<0.05$;, $p<0.01$;*, $p<0.001$ by Student's t-test. NS=non-significant.

FIG. 4A is a graph plotting the bodyweight of db/db mice (in grams) as a function of time (days) for treatment with celastrol (vehicle control (diamond trace), 100 μg/kg celastrol in 25 μL DMSO by i.p. once a day (square trace)). FIG. 4B is a bar graph illustrating the food intake (in grams/day) of db/db mice during the course of treatment with celastrol (left bar, vehicle control; right bar, 100 μg/kg celastrol by i.p. once a day). FIG. 4C is a bar graph illustrating the 6 hour fasting blood glucose level (in mg/dL) of db/db mice at the end of two weeks of treatment with celastrol (left bar, vehicle control; right bar, 100 μg/kg celastrol by i.p. once a day). In all cases, n=5 mice per group.

FIG. 5A is a graph plotting the bodyweight of HFD-fed obese mice (in grams) as a function of time (days) for treatment with celastrol (vehicle control (diamond trace), 10 mg/kg celastrol orally once a day (square trace)). FIG. 5B is a bar graph illustrating the food intake (in grams/day) of HFD-fed obese mice during the course of treatment with celastrol (left bar, vehicle control; right bar, 10 mg/kg celastrol orally once a day). FIG. 5C is a bar graph illustrating the 6 hour fasting blood glucose level (in mg/dL) of HFD-fed obese mice at the end of two weeks of treatment with celastrol (left bar, vehicle control; right bar, 10 mg/kg celastrol orally once a day). FIG. 5D is a graph plotting the bodyweight of lean mice (in grams) as a function of time (days) for treatment with celastrol (vehicle control (diamond trace), 10 mg/kg celastrol orally once a day (square trace)). FIG. 5E is a bar graph illustrating the food intake (in grams/day) of lean mice during the course of treatment with celastrol (left bar, vehicle control; right bar, 10 mg/kg celastrol orally once a day). FIG. 5F is a bar graph illustrating the 6 hour fasting blood glucose level (in mg/dL) of lean mice at the end of two weeks of treatment with celastrol (left bar, vehicle control; right bar, 10 mg/kg celastrol orally once a day). In all cases, n=5 mice per group. *, $p<0.05$;, $p<0.01$;*, $p<0.001$ by Student's t-test.

FIG. 6A is a graph plotting the bodyweight of ob/ob mice (in grams) as a function of time (days) for treatment with celastrol (vehicle control (triangle trace), 10 mg/kg celastrol orally once a day (square trace)). FIG. 6B is a graph plotting the bodyweight of db/db mice (in grams) as a function of time (days) for treatment with celastrol (vehicle control (triangle trace), 10 mg/kg celastrol orally once a day (square trace)). FIG. 6C is a bar graph illustrating the food intake (in grams/day) of ob/ob mice during the course of treatment with celastrol (left bar, vehicle control; right bar, 10 mg/kg celastrol orally once a day). FIG. 6D is a bar graph illustrating the food intake (in grams/day) of db/db mice at the end of two weeks of treatment with celastrol (left bar, vehicle control; right bar, 10 mg/kg celastrol orally once a day).

FIG. 7A is a graph plotting the cumulative food intake of HFD-fed obese mice (in grams) as a function of time (hours) upon treatment with celastrol alone, leptin alone, and celastrol and leptin in combination (vehicle control (DMSO+saline, diamond trace), leptin alone (square trace), celastrol alone (triangle trace), and both celastrol and leptin (cross (-x-) trace)). FIG. 7B is a bar graph plotting the percent decrease in food intake in both lean and HFD-fed mice 6-hours post leptin injection (left to right, lean mice without celastrol, lean mice with celastrol, HFD-fed obese mice without celastrol, and HFD-fed mice with celastrol). FIG. 7C is a graph plotting the cumulative food intake of lean mice (in grams) as a function of time (hours) upon treatment with celastrol alone, leptin alone, and celastrol and leptin in combination (vehicle control (DMSO+saline, diamond trace), leptin alone (square trace), celastrol alone (triangle trace), and both celastrol and leptin (cross (-x-) trace)). FIG. 7D is a bar graph plotting the change in body weight (in grams) over a 24 hour period in both lean and HFD-fed obese mice upon treatment with celastrol alone, leptin alone, and celastrol and leptin in combination (left to right, lean mice with vehicle control (DMSO+saline), lean mice leptin alone, lean mice celastrol alone, lean mice treated with both celastrol and leptin, HFD-fed obese mice with vehicle control (DMSO+saline), HFD-fed obese mice leptin alone, HFD-fed obese mice celastrol alone, HFD-fed obese mice treated with both celastrol and leptin). In all cases, n=3 mice per group.

FIG. 8A is a bar graph illustrating the lean mass (in grams) of HFD-fed obese mice as measured using dual-emission x-ray absorptiometry (DEXA) following two weeks of treatment with celastrol at different doses (from left to right, vehicle control, 10 µg/kg celastrol by i.p. once a day, 50 µg/kg celastrol by i.p. once a day, and 100 µg/kg celastrol by i.p. once a day). FIG. 8B is a bar graph illustrating the fat mass (in grams) of HFD-fed obese mice as measured using DEXA following two weeks of treatment with celastrol at different doses (from left to right, vehicle control, 10 µg/kg celastrol by i.p. once a day, 50 µg/kg celastrol by i.p. once a day, and 100 µg/kg celastrol by i.p. once a day). FIG. 8C is a bar graph illustrating the percent body fat of HFD-fed obese mice as measured using DEXA following two weeks of treatment with celastrol at different doses (from left to right, vehicle control, 10 µg/kg celastrol by i.p. once a day, 50 µg/kg celastrol by i.p. once a day, and 100 µg/kg celastrol by i.p. once a day). FIG. 8D is a graph plotting the plasma leptin level (in ng/mL) measured using a leptin specific ELISA kit as a function of time (days) of treatment with celastrol (vehicle control (diamond trace), 100 µg/kg celastrol by i.p. once a day (square trace)).

FIG. 9A is a graph plotting the plasma blood glucose levels in HFD fed mice undergoing a glucose tolerance test (GTT) at day 7 as a function of time (minutes) following the injection of D-glucose (vehicle control (diamond trace), 100 µg/kg celastrol by i.p. once a day (square trace)). FIG. 9B is a bar graph plotting the area under the curve (AUC, in min mg/dL) for the traces in FIG. 9A for both the vehicle control (left bar) and celastrol (100 µg/kg celastrol, right bar). FIG. 9C is a graph plotting the plasma blood glucose levels in HFD fed mice undergoing an insulin tolerance test (ITT) at day 7 as a function of time (minutes) following the injection of insulin (vehicle control (diamond trace), 100 µg/kg celastrol by i.p. once a day (square trace)). FIG. 9D is a bar graph plotting the area under the curve (AUC, in min mg/dL) for the traces in FIG. 9C for both the vehicle control (left bar) and celastrol (100 µg/kg celastrol, right bar). In all cases, n=5 mice per group. *, $p<0.05$;, $p<0.01$;*, $p<0.001$ by Student's t-test.

FIG. 10A is a bar graph illustrating the level of hepatic mRNA expression of glucose 6-phosphatase (G6pase, in arbitrary units) in HFD-fed obese mice following treatment with celastrol for three weeks (left bar, vehicle control; right bar, celastrol administration). FIG. 10B is a bar graph illustrating the level of hepatic mRNA expression of phosphoenolpyruvate carboxykinase (PEPCK, in arbitrary units) in HFD-fed obese mice following treatment with celastrol for three weeks (left bar, vehicle control; right bar, celastrol administration). FIG. 10C is a bar graph illustrating the level of hepatic mRNA expression of peroxisome proliferator-activated receptor gamma coactivator 1-alpha (PGC1a, in arbitrary units) in HFD-fed obese mice following treatment with celastrol for three weeks (left bar, vehicle control; right bar, celastrol administration).

FIG. 11A is a bar graph plotting the serum level of ALT (U/L) in HFD-fed obese mice following treatment with celastrol for three weeks (left bar, vehicle control; right bar, celastrol administration). FIG. 11B is a bar graph plotting the serum level of AST (U/L) in HFD-fed obese mice following treatment with celastrol for three weeks (left bar, vehicle control; right bar, celastrol administration). In all cases, n=5 mice per group. *, p<0.05;, p<0.01;*, p<0.001 by Student's t-test.

FIG. 12A is a bar graph plotting the serum level of T3 (ng/ml) in HFD-fed obese mice following treatment with celastrol for three weeks (left bar, vehicle control; right bar, celastrol administration). FIG. 12B is a bar graph plotting the serum level of T4 (ng/mL) in HFD-fed obese mice following treatment with celastrol for three weeks (left bar, vehicle control; right bar, celastrol administration). In all cases, n=5 mice per group. *, p<0.05; , p<0.01;*, p<0.001 by Student's t-test.

DETAILED DESCRIPTION OF THE INVENTION

I. Definitions

Figure 1A:
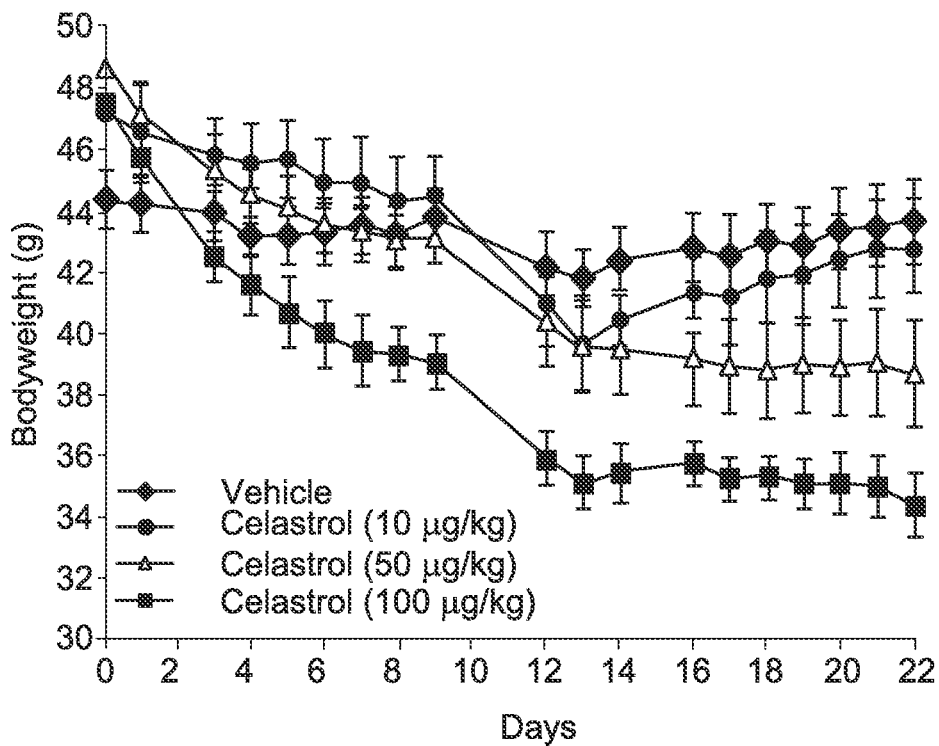
FIGS. 1A-D illustrate the effect of celastrol, administered intraperitoneally (i.p.), on the food intake, body weight, and blood glucose levels of high fat diet-fed (HFD-fed) obese mice.

"Analog" and "Derivative", are used herein interchangeably, and refer to a compound that possesses the same pentacyclic core as a parent compound, but differs from the parent compound in bond order, in the absence or presence of one or more atoms and/or groups of atoms, and combinations thereof. The derivative can differ from the parent compound, for example, in one or more substituents present on the pentacyclic core, which may include one or more atoms, functional groups, or substructures. The derivative can also differ from the parent compound in the bond order between atoms within the pentacyclic core. In general, a derivative can be imagined to be formed, at least theoretically, from the parent compound via chemical and/or physical processes. For example, derivatives of celastrol include compounds possessing one or more substituents affixed to the pentacyclic celastrol core.

"Co-administration", as used herein, includes simultaneous and sequential administration. An appropriate time course for sequential administration may be chosen by the physician, according to such factors as the nature of a patient's illness, and the patient's condition.

"Pharmaceutically acceptable", as used herein, refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_5$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Obese," as used herein, refers to a patient having a body mass index of greater than 30 kg/m². "Overweight" and "Pre-Obese," as used herein, refer to patients having a body mass index of greater than 25 kg/m². "Morbidly Obese," as used herein, refers to a patient having a body mass index of greater than 40 kg/m², a body mass index of greater than 35 kg/m² in combination with one or more co-morbidities, a body mass index of greater than 30 kg/m² in combination with uncontrollable diabetes, or combinations thereof.

"Effective amount" or "therapeutically effective amount", as used herein, refers to an amount of a weight loss agent that is effective to induce weight loss in a pre-obese, obese, or morbidly obese patient, reduce body fat in a pre-obese, obese, or morbidly obese patient, reduce food intake in a pre-obese, obese, or morbidly obese patient, improve glucose homeostasis in a pre-obese, obese, or morbidly obese patient, prevent weight gain and/or prevent an increase in body mass index in a normal, pre-obese, obese, or morbidly obese patient, or combinations thereof.

II. Weight Loss Agents

Pentacyclic triterpenes that can be administered to promote weight loss, reduce body fat, reduce food intake, improve glucose homeostasis, or combinations thereof are provided herein.

In certain embodiments, the weight loss agent is a compound defined by Formula I

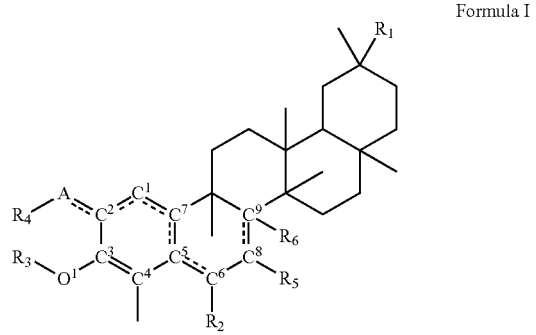

Formula I wherein
the dotted lines between A and $C^2$, $C^1$ and $C^2$, $C^1$ and $C^7$, $C^7$ and $C^5$, $C^5$ and $C^6$, and $C^8$ and $C^9$ indicate that a single or double bond may be present, as valence permits;

$R_1$ is a carboxylic acid (—COOH), primary amide (e.g., —CONH$_2$), secondary amide (e.g., —CONHR$_7$), tertiary amide (e.g., —CONR$_7$R$_7$), secondary carbamate (e.g., —OCONHR$_7$; —NHCOOR$_7$), tertiary carbamate (e.g., —OCONR$_7$R$_7$; —NR—COOR$_7$), urea (e.g., —NHCONHR$_7$; —NR$_7$CONHR$_7$; —NHCONR$_7$R$_7$, —NR$_7$CONR$_7$R$_7$), carbinol (e.g., —CH$_2$OH; —CHR$_7$OH, —CR$_7$R$_7$OH), ether (e.g., —OR$_7$), ester (e.g., —COOR$_7$), alcohol (—OH), thiol (—SH), primary amine (—NH$_2$), secondary amine (e.g., —NHR$_7$), tertiary amine (e.g., —NR$_7$R$_7$), thioether (e.g., —SR$_7$), sulfinyl group (e.g., —SOR$_7$), sulfonyl group (e.g., —SOOR$_7$), sulfino group, halogen, nitrile, or CF$_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, CF$_3$, ester, amide, urea, carbamate, thioether, carboxylic acid, and aryl;

$R_2$ is hydrogen; hydroxy (—OH), thiol (—SH), ether (e.g., —OR$_7$), thioether (e.g., —SR$_7$), primary amine (—NH$_2$), secondary amine (e.g., —NHR$_7$), tertiary amine (e.g., —NR$_7$R$_7$), primary amide (e.g., —CONH$_2$), secondary amide (e.g., —NHCOR$_7$), tertiary amide (e.g., —NR—COR$_7$), secondary carbamate (e.g., —OCONHR$_7$; —NHCOOR$_7$), tertiary carbamate (e.g., —OCONR$_7$R$_7$; —NR$_7$COOR$_7$), urea (e.g., —NHCONHR$_7$; —NR$_7$CONHR$_7$; —NHCONR$_7$R$_7$, —NR$_7$CONR$_7$R$_7$), sulfinyl group (e.g., —SOR$_7$), sulfonyl group (e.g., —SOOR$_7$) sulfino group, halogen, nitrile, or CF$_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, CF$_3$, ester, amide, urea, carbamate, thioether, carboxylic acid, and aryl;

A is nitrogen or oxygen when a double bond is present between A and $C^2$, or oxygen or NR when a single bond is present between A and $C^2$, wherein R is defined the same $R_1$;

$R_3$ is hydrogen, a carbonyl group (e.g., —COR$_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, CF$_3$, ester, amide, urea, carbamate, thioether, carboxylic acid, and aryl;

$R_4$ is absent when A is oxygen and a double bond is present between A and $C^2$, a hydroxy (—OH) group when A is nitrogen and a double bond is present between A and $C^2$, or is hydrogen, a carbonyl group (e.g., —COR$_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, CF$_3$, ester, amide, urea, carbamate, thioether, carboxylic acid, and aryl when A is oxygen or NR and a single bond is present between A and $C^2$; or A is oxygen or NR, a single bond is present between A and $C^2$, and $R_3$ and $R_4$, taken together with A, $C^2$, $C^3$, and $O^1$, form a 5- to 7-membered ring optionally substituted with between one and four substituents individually selected from alkyl, cyclopropyl, cyclobutyl ether, amine, halogen, hydroxyl, ether, nitrile, $CF_3$, ester, amide, urea, carbamate, thioether, and carboxylic acid;

$R_5$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —$NR_7COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_6$ is absent when a double bond is present between $C^8$ and $C^9$, is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —$NR_7COR_7$), secondary carbamate (e.g., —$OCONHR_7$; —$NHCOOR_7$), tertiary carbamate (e.g., —$OCONR_7R_7$; —NR $COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when a single bond is present between $C^8$ and $C^9$; or a single bond is present between $C^8$ and $C^9$, and $R_5$ and $R_6$, taken together with $C_8$ and $C_9$, form a cyclopropyl or epoxide ring; and $R_7$, when present, is individually for each occurrence an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

or a pharmaceutically acceptable salt or prodrug thereof.

In particular embodiments of Formula I, the weight loss agent is a compound defined by the structure shown below

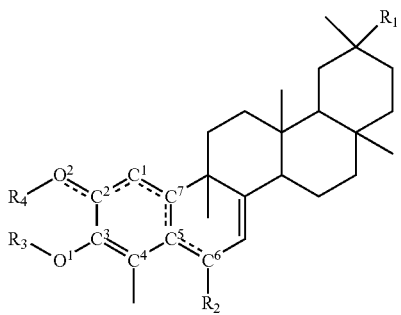

wherein
the dotted lines between $O^2$ and $C^2$, $C^1$ and $C^2$, $C^1$ and $C^7$, $C^7$ and $C^5$, and $C^5$ and $C^6$ indicate that a single or double bond may be present, as valence permits;

$R_1$ is a carboxylic acid (—COOH), primary amide (e.g., —$CONH_2$), secondary amide (e.g., —$CONHR_7$), tertiary amide (e.g., —$CONR_7R_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), carbinol (e.g., —$CH_2OH$; —$CHR_7OH$, —$CR_7R_7OH$), ether (e.g., —$OR_7$), ester (e.g., —$COOR_7$), alcohol (—OH), thiol (—SH), primary amine (—$NH_2$), secondary amine (e.g., —$NHR_7$), tertiary amine (e.g., —$NR_7R_7$), thioether (e.g., —$SR_7$), sulfinyl group (e.g., —$SOR_7$), sulfonyl group (e.g., —$SOOR_7$), sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_2$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_3$ is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, $R_4$ is absent when a double bond is present between $O^2$ and $C^2$, or is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when a single bond is present between $O^2$ and $C^2$; or a single bond is present between $O^2$ and $C^2$, and $R_3$ and $R_4$, taken together with $O^2$, $C^2$, $C^3$, and $O^1$, form a 5- to 7-membered ring optionally substituted with between one and four substituents individually selected from alkyl, cyclopropyl, cyclobutyl ether, amine, halogen, hydroxyl, ether, nitrile, $CF_3$, ester, amide, urea, carbamate, thioether, and carboxylic acid; and $R_7$, when present, is individually for each occurrence an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

or a pharmaceutically acceptable salt or prodrug thereof.

In some embodiments of Formula I, a double bond is present between A and $C^2$, $C^1$ and $C^7$, $C^5$ and $C^6$, and $C^8$ and $C^9$, and a single bond is present between $C^1$ and $C^2$, and $C^7$ and $C^5$. In other embodiments of Formula I, a double bond is present between $C^1$ and $C^2$, $C^7$ and $C^5$, and $C^8$ and Co, and a single bond is present between A and $C^2$, $C^1$ and $C^7$, and $C^5$ and $C^6$.

In particular embodiments of Formula I, $R_1$ is a carboxylic acid, ester, or amide; $R_2$ is hydrogen, an ether (—$OR_7$) or thioether (—$SR_7$); and $R_7$ is a $C^1$-$C^{12}$, more preferably $C^1$-$C^8$ alkyl group optionally substituted with between one and three substituents individually selected from alkyl, amine, halogen, hydroxyl, ester, amide, and carboxylic acid.

In particular embodiments, the weight loss agent is a compound defined by Formula II Formula II

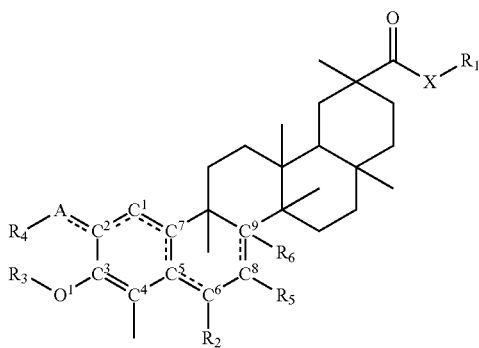

wherein
the dotted lines between A and $C^2$, $C^1$ and $C^2$, $C^1$ and $C^7$, $C^7$ and $C^5$, $C^5$ and $C^6$, and $C^8$ and $C^9$ indicate that a single or double bond may be present, as valence permits;

X is —O—, —$NR_7$—, —S—, —SO—, or —$SO_2$—;

$R_1$ is hydrogen, or an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, and aryl;

$R_2$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —$NR_7COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

A is nitrogen or oxygen when a double bond is present between A and $C^2$, or oxygen or NR when a single bond is present between A and $C^2$;

$R_3$ is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_4$ is absent when A is oxygen and a double bond is present between A and $C^2$, a hydroxy (—OH) group when A is nitrogen and a double bond is present between A and $C^2$, or is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when A is oxygen or NR and a single bond is present between A and $C^2$; or A is oxygen or nitrogen, a single bond is present between A and $C^2$, and $R_3$ and $R_4$, taken together with A, $C^2$, $C^3$, and $O^1$, form a 5- to 7-membered ring optionally substituted with between one and four substituents individually selected from alkyl, cyclopropyl, cyclobutyl ether, amine, halogen, hydroxyl, ether, nitrile, $CF_3$, ester, amide, urea, carbamate, thioether, and carboxylic acid;

$R_5$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —$NR_7COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_6$ is absent when a double bond is present between $C^8$ and $C^9$, is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —NR—$COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when a single bond is present between $C^8$ and $C^9$; or a single bond is present between $C^8$ and $C^9$, and $R_5$ and $R_6$, taken together with $C_8$ and $C^9$, form a cyclopropyl or epoxide ring; and $R_7$, when present, is individually for each occurrence an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, or a pharmaceutically acceptable salt or prodrug thereof.

In some embodiments of Formula II, a double bond is present between A and $C^2$, $C^1$ and $C^7$, $C^1$ and $C^6$, and $C^8$ and $C^9$, and a single bond is present between $C^1$ and $C^2$, and $C^7$ and $C^5$. In other embodiments of Formula II, a double bond is present between $C^1$ and $C^2$, $C^7$ and $C^5$, and $C^8$ and $C^9$, and a single bond is present between A and $C^2$, $C^1$ and $C^7$, and $C^5$ and $C^6$.

In some embodiments of Formula II, X is O or —$NR_7$—; $R_1$ is hydrogen or alkyl group optionally substituted with between one and three substituents individually selected from alkyl, amine, halogen, hydroxyl, ester, amide, and carboxylic acid; $R_2$ is hydrogen, an ether (—$OR_7$) or thioether (—$SR_7$); and $R_7$ is, individually for each occurrence, a $C^1$-$C^{12}$, more preferably $C^1$-$C^8$ alkyl group optionally substituted with between one and three substituents individually selected from alkyl, amine, halogen, hydroxyl, ester, amide, and carboxylic acid.

In particular embodiments, the weight loss agent is a compound defined by the structure shown below

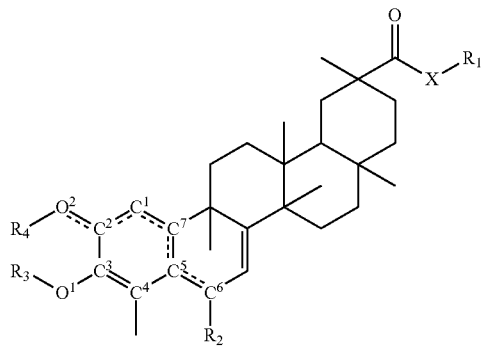

wherein the dotted lines between $O^2$ and $C^2$, $C^1$ and $C^2$, $C^1$ and $C^7$, $C^7$ and $C^5$, and $C^5$ and $C^6$, indicate that a single or double bond may be present, as valence permits;

X is —O—, —$NR_7$—, —S—, —SO—, or —$SO_2$—;

$R_1$ is hydrogen, or an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, and aryl;

$R_2$ is hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —NR—$COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_3$ is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

$R_4$ is absent when a double bond is present between $O^2$ and $C^2$, or is hydrogen, a carbonyl group (e.g., —$COR_7$), or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl when a single bond is present between $O^2$ and $C^2$; or a single bond is present between $O^2$ and $C^2$, and $R_3$ and $R_4$, taken together with $O^2$, $C^2$, $C^3$, and $O^1$, form a 5- to 7-membered ring optionally substituted with between one and four substituents individually selected from alkyl, cyclopropyl, cyclobutyl ether, amine, halogen, hydroxyl, ether, nitrile, $CF_3$, ester, amide, urea, carbamate, thioether, and carboxylic acid; and $R_7$, when present, is individually for each occurrence an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

or a pharmaceutically acceptable salt or prodrug thereof.

In some embodiments of Formula II, a double bond is present between A and $C^2$, $C^1$ and $C^7$, $C^5$ and $C^6$, and $C^8$ and Co, and a single bond is present between $C^1$ and $C^2$, and $C^7$ and $C^5$. In other embodiments of Formula II, a double bond is present between $C^1$ and $C^2$, $C^7$ and $C^5$, and $C^8$ and $C_0$, and a single bond is present between A and $C^2$, $C^1$ and $C^7$, and $C^5$ and $C^6$.

In some embodiments of Formula II, X is O or —NR$_7$—; R$_1$ is hydrogen or alkyl group optionally substituted with between one and three substituents individually selected from alkyl, amine, halogen, hydroxyl, ester, amide, and carboxylic acid; R$_2$ is hydrogen, an ether (—OR$_7$) or thioether (—SR$_7$); and R$_7$ is, individually for each occurrence, a $C^1$-$C^{12}$, more preferably $C^1$-$C^8$ alkyl group optionally substituted with between one and three substituents individually selected from alkyl, amine, halogen, hydroxyl, ester, amide, and carboxylic acid.

The weight loss agents may have one or more chiral centers, and thus can exist as one or more stereoisomers. Such stereoisomers can exist as a single enantiomer, a mixture of enantiomers, a mixture of diastereomers, or a racemic mixture.

As used herein, the term "stereoisomers" refers to compounds made up of the same atoms having the same bond order but having different three-dimensional arrangements of atoms that are not interchangeable. The three-dimensional structures are called configurations. As used herein, the term "enantiomers" refers to two stereoisomers that are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

In some embodiments, the compounds described herein have the following stereochemistry:

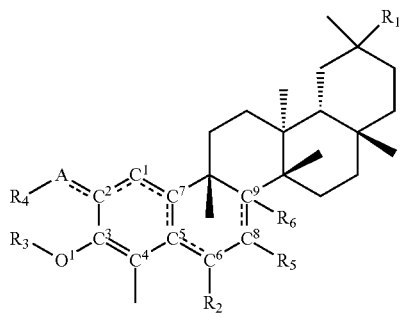

or

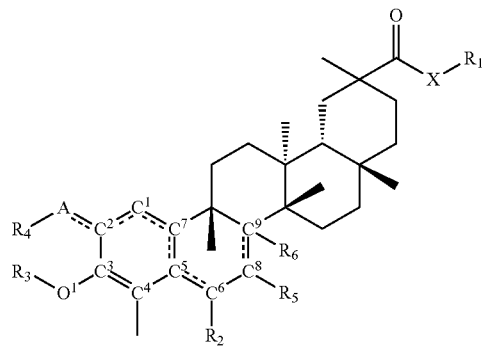

In particular embodiments, the weight loss agent is one of the following

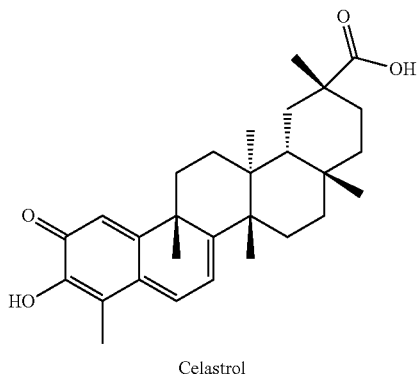

Celastrol

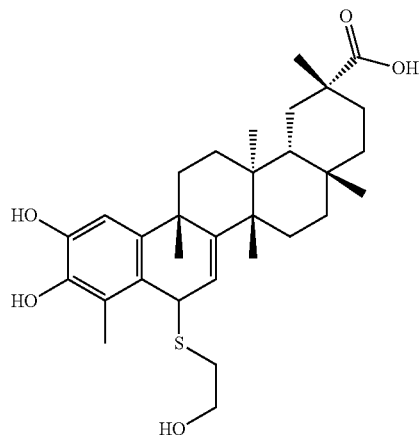

mCS1

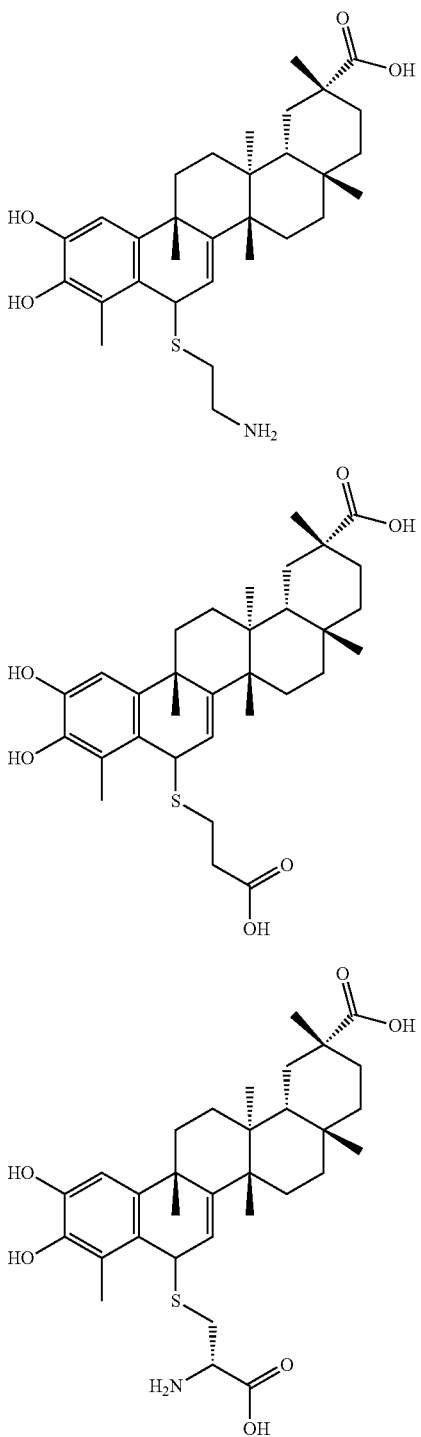

mCS2 mCS3 mCS4

The weight loss agent can also be a pharmaceutically acceptable salt of any of the compounds described above. In some cases, it may be desirable to prepare the salt of a compound described above due to one or more of the salt's advantageous physical properties, such as enhanced stability or a desirable solubility or dissolution profile.

Generally, pharmaceutically acceptable salts can be prepared by reaction of the free acid or base forms of a compound described above with a stoichiometric amount of the appropriate base or acid in water, in an organic solvent, or in a mixture of the two. Generally, non-aqueous media including ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, M D, 2000, p. 704; and "Handbook of Pharmaceutical Salts: Properties, Selection, and Use," P. Heinrich Stahl and Camille G. Wermuth, Eds., Wiley-VCH, Weinheim, 2002.

Suitable pharmaceutically acceptable acid addition salts include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids.

Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, ß-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt may include alkali metal salts, including sodium or potassium salts; alkaline earth metal salts, e.g., calcium or magnesium salts; and salts formed with suitable organic ligands, e.g., quaternary ammonium salts. Base salts can also be formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may also be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

The weight loss agent can also be a pharmaceutically acceptable prodrug of any of the compounds described above. Prodrugs are compounds that, when metabolized in vivo, undergo conversion to compounds having the desired pharmacological activity. Prodrugs can be prepared by replacing appropriate functionalities present in the compounds described above with "pro-moieties" as described, for example, in H. Bundgaar, Design of Prodrugs (1985). Examples of prodrugs include ester, ether or amide derivatives of the compounds described above, polyethylene glycol derivatives of the compounds described above, N-acyl amine derivatives, dihydropyridine pyridine derivatives, amino-containing derivatives conjugated to polypeptides, 2-hydroxybenzamide derivatives, carbamate derivatives, N-oxides derivatives that are biologically reduced to the active amines, and N-mannich base derivatives. For further discussion of prodrugs, see, for example, Rautio, J. et al. *Nature Reviews Drug Discovery.* 7:255-270 (2008).

A. Methods of preparation

The weight loss agents described above can be prepared using methods known in the art. Representative methodologies for the preparation of certain active agents are described below. The appropriate route for synthesis of a given weight loss agent can be selected in view of the structure of the compound as a whole as it relates to compatibility of functional groups, protecting group strategies, and the presence of labile bonds. In addition to the synthetic methodologies discussed below, alternative reactions and strategies useful for the preparation of the creatine compounds disclosed herein are known in the art. See, for example, March, "Advanced Organic Chemistry," 5th Edition, 2001, Wiley-Interscience Publication, New York).

Celastrol can be obtained from commercial sources, or isolated from plants, e.g. Tripterygium wilfordii, by methods known in the art. See, for example, Kutney, *Can. J. Chem.* 59:2677 (1981) and Zhang, W., et al., *Acta Pharm. Sin.* 21:592 (1986). Celastrol can serve as a convenient starting material for compounds of Formula I and Formula II.

By way of exemplification, compounds of Formula I wherein $R_1$ is an ester can be prepared by reacting celastrol with a suitable alcohol in the presence of acid or base catalyst. For example, treatment of celastrol with excess ethanol in the presence of an acid catalyst can afford compounds of Formula I where $R_1$ is an ethyl ester (—$COOR_5$). Other ester derivatives can be similarly prepared using appropriate alcohol starting materials. Similarly, compounds of Formula I wherein $R_1$ is an amide can be prepared by reacting celastrol with a suitable amine under standard amide bond-forming conditions (e.g., in the presence of a carbodiimide dehydrating agent, such as N,N'-dicyclohexylcarbodiimide (DCC), N,N'-Diisopropylcarbodiimide (DIC), or 1-Ethyl-3-(3-dimethylaminopropyl) carbodiimide (EDC) and a base, such as DMAP or triethylamine).

Compounds of Formula I where $R_2$ is other than hydrogen may be prepared using a Michael-type reaction. For example, compounds of Formula I wherein $R_2$ is a thioether can be prepared by reaction of celastrol with a suitably nucleophilic thiol.

III. Pharmaceutical Formulations

Pharmaceutical formulations are provided containing a therapeutically effective amount of a weight loss agent described herein, or a pharmaceutically acceptable salt or prodrug thereof, in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials that are generally recognized as safe (GRAS), and may be administered to an individual without causing undesirable biological side effects or unwanted interactions.

A. Additional Therapeutics

In some cases, the pharmaceutical formulation can further contain one or more additional active agents.

In certain embodiments, the pharmaceutical formulations further contain leptin, a leptin analog, or combinations thereof.

Leptin is a peptide hormone that serves as the afferent signal in a negative feedback loop regulating food intake and body weight in vivo. Unprocessed human leptin is synthesized in vivo as a 167 amino acid, 16 kDa protein prohormone. Unprocessed leptin includes an N-terminal 21-amino acid signal sequence that is cleaved from the remainder of the polypeptide to generate mature, circulating, leptin (containing 146 amino acids).

The terms "leptin" and "leptin analog," as used herein, encompass naturally occurring human leptin, naturally occurring leptin produced by a non-human species such as a mouse or rat, recombinantly produced mature leptin, such as metreleptin (i.e., recominbinant methionyl human leptin or r-metHuLeptin, which is a 147 amino acid leptin analog generated by the genetically engineered N-terminal addition of a methionine to the N-terminal amino acid of the 146-amino acid, mature, circulating, human leptin), as well as leptin fragments, leptin variants, leptin fusion proteins, and other derivatives thereof known in the art to possess biological activity.

Exemplary leptin analogs and derivatives include those described in International Patent Publication Nos. WO 96/05309, WO 96/40912; WO 97/06816, WO 00/20872, WO 97/18833, WO 97/38014, WO 98/08512, WO 98/12224, WO 98/28427, WO 98/46257, WO 98/55139, WO 00/09165, WO 00/47741, WO 2004/039832, WO 97/02004, and WO 00/21574; International Patent Applicant Nos. PCT/US96/22308 and PCT/US96/01471; U.S. Pat. Nos. 5,521,283, 5,532,336, 5,552,524, 5,552,523, 5,552,522, 5,935,810, 6,001,968, 6,429,290, 6,350,730, 6,936,439, 6,420,339, 6,541,033, 7,112,659, 7,183,254, and 7,208,577, and U.S. Patent Publication Nos. 2005/0176107, 2005/0163799. Exemplary leptin variants include those where the amino acid at position 43 is substituted with Asp or Glu; position 48 is substituted Ala; position 49 is substituted with Glu, or absent; position 75 is substituted with Ala; position 89 is substituted with Leu; position 93 is substituted with Asp or Glu; position 98 is substituted with Ala; position 117 is substituted with Ser, position 139 is substituted with Leu, position 167 is substituted with Ser, and any combination thereof.

In certain embodiments, the pharmaceutical formulation includes r-metHuLeptin (A-100, METRELEPTIN®), available from Amylin Pharmaceuticals (San Diego, Calif.).

Pharmaceutical formulations can also include one or more vitamins, minerals, dietary supplements, nutraceutical agents, such as proteins, carbohydrates, amino acids, fatty acids, antioxidants, and plant or animal extracts, or combinations thereof. Suitable vitamins, minerals, nutraceutical agents, and dietary supplements are known in the art, and disclosed, for example, in Roberts et al., (*Nutriceuticals: The Complete Encyclopedia of Supplements, Herbs, Vitamins, and Healing Foods*, American Nutriceutical Association, 2001). Nutraceutical agents and dietary supplements are also disclosed in *Physicians' Desk Reference for Nutritional Supplements,* 1st Ed. (2001) and *The Physicians' Desk Reference for Herbal Medicines,* 1st Ed. (2001).

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions that include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

1. Controlled Release Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Formulations

The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl-celluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one embodiment, the acrylic polymer is an acrylic resin lacquer such as that which is commercially available from Rohm Pharma under the tradename EUDRAGIT® In further preferred embodiments, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT®. RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids. The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT®RL, 50% EUDRAGIT® RL and 50% EUDRAGIT® RS, and 10% EUDRAGIT® RL and 90% EUDRAGIT® RS. One skilled in the art will recognize that other acrylic polymers may also be used, such as, for example, EUDRAGIT®.L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Formulations

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT'R (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITs® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac.

Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release

The formulation can provide pulsatile delivery of the one or more of the compounds disclosed herein. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

C. Parenteral Formulations

The compounds can be formulated for parenteral administration. "Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

Nano- and Microparticles

For parenteral administration, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles that provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers that are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material that is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins that are water insoluble, such as zein, can also be used as materials for the formation of drug containing microparticles. Additionally, proteins, polysaccharides and combinations thereof that are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations that cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Depot Formulations

Active agents can be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection.

A variety of carriers may be incorporated into the depot formulation to provide for the controlled release of the active agent. In some cases, depot formulations contain one or more biodegradable polymeric or oligomeric carriers. Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), polyglycolide (PGA), poly-3-hydroxybutyrate (PHB) and copolymers thereof, poly-4-hydroxybutyrate (P4HB), polycaprolactone, cellulose, hydroxypropyl methylcellulose, ethylcellulose, as well as blends, derivatives, copolymers, and combinations thereof.

In depot formulations containing a polymeric or oligomeric carrier, the carrier and active agent can be formulated as a solution, an emulsion, or suspension. One or more weight loss agents, and optionally one or more additional active agents, can also be incorporated into polymeric or oligomeric microparticles, nanoparticles, or combinations thereof.

In some cases, the formulation is fluid and designed to solidify or gel (i.e., forming a hydrogel or organogel) upon injection. This can result from a change in solubility of the composition upon injection, or for example, by injecting a pre-polymer mixed with an initiator and/or crosslinking agent. The polymer matrix, polymer solution, or polymeric particles entrap the active agent at the injection site. As the polymeric carrier is gradually degraded, the active agent is released, either by diffusion of the agent out of the matrix and/or dissipation of the matrix as it is absorbed. The release rate of the active agent from the injection site can be controlled by varying, for example, the chemical composition, molecular weight, crosslink density, and/or concentration of the polymeric carrier. Examples of such systems include those described in U.S. Pat. Nos. 4,938,763, 5,480, 656 and 6,113,943.

Depot formulations can also be prepared by using other rate-controlling excipients, including hydrophobic materials, including acceptable oils (e.g., peanut oil, corn oil, sesame oil, cottonseed oil, etc.) and phospholipids, ion-exchange resins, and sparingly soluble carriers.

The depot formulation can further contain a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the weight loss agents as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Implants

Implantation of a slow-release or sustained-release system, such that a constant level of dosage is maintained is also contemplated herein. In such cases, the active agent(s) provided herein can be dispersed in a solid matrix optionally coated with an outer rate-controlling membrane. The compound diffuses from the solid matrix (and optionally through the outer membrane) sustained, rate-controlled release. The solid matrix and membrane may be formed from any suitable material known in the art including, but not limited to, polymers, bioerodible polymers, and hydrogels.

C. Pulmonary Formulations

The compounds described herein can be formulated for parenteral administration. Pharmaceutical formulations and methods for the pulmonary administration are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

The alveolar surface area is the largest in the respiratory system and is where drug absorption occurs. The alveoli are covered by a thin epithelium without cilia or a mucus blanket and secrete surfactant phospholipids. Effective delivery of therapeutic agents via pulmonary routes requires that the active agent be formulated so as to reach the alveoli.

In the case of pulmonary administration, formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

Useful formulations, and methods of manufacture, are described by Caryalho, et al., J Aerosol Med Pulm Drug Deliv. 2011 April; 24(2):61-80. Epub 2011 Mar. 16, for delivery of chemotherapeutic drugs to the lungs.

1. Dry Powder Formulations

Dry powder formulations are finely divided solid formulations containing one or more active agents which are suitable for pulmonary administration. In dry powder formulations, the one or more active agents can be incorporated in crystalline or amorphous form.

Dry powder formulations can be administered via pulmonary inhalation to a patient without the benefit of any carrier, other than air or a suitable propellant. Preferably, however, the dry powder formulations include one or more pharmaceutically acceptable carriers.

The pharmaceutical carrier may include a bulking agent, such as carbohydrates (including monosaccharides, polysaccharides, and cyclodextrins), polypeptides, amino acids, and combinations thereof. Suitable bulking agents include fructose, galactose, glucose, lactitol, lactose, maltitol, maltose, mannitol, melezitose, myoinositol, palatinite, raffinose, stachyose, sucrose, trehalose, xylitol, hydrates thereof, and combinations thereof.

The pharmaceutical carrier may include a lipid or surfactant. Natural surfactants such as dipalmitoylphosphatidylcholine (DPPC) are the most preferred. This is commercially available for treatment of respiratory distress syndrome in premature infants. Synthetic and animal derived pulmonary surfactants include:

Synthetic Pulmonary Surfactants

Exosurf—a mixture of DPPC with hexadecanol and tyloxapol added as spreading agents Pumactant (Artificial Lung Expanding Compound or ALEC)—a mixture of DPPC and PG KL-4—composed of DPPC, palmitoyl-oleoyl phosphatidylglycerol, and palmitic acid, combined with a 21 amino acid synthetic peptide that mimics the structural characteristics of SP-B.

Venticute—DPPC, PG, palmitic acid and recombinant SP—C Animal derived surfactants Alveofact—extracted from cow lung lavage fluid Curosurf—extracted from material derived from minced pig lung Infasurf—extracted from calf lung lavage fluid Survanta—extracted from minced cow lung with additional DPPC, palmitic acid and tripalmitin Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more active agents with a pharmaceutical carrier. Optionally, additional active agents may be incorporated into the mixture. The mixture is then formed into particles suitable for pulmonary administration using techniques known in the art, such as lyophilization, spray drying, agglomeration, spray coating, extrusion processes, hot melt particle formation, phase separation particle formation (spontaneous emulsion particle formation, solvent evaporation particle formation, and solvent removal particle formation), coacervation, low temperature casting, grinding, milling (e.g., air-attrition milling (jet milling), ball milling), high pressure homogenization, and/or supercritical fluid crystallization.

An appropriate method of particle formation can be selected based on the desired particle size, particle size distribution, and particle morphology. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung as well as uptake of the drug particles. As discussed above, drug particles should reach the alveoli to maximize therapeutic efficacy. Accordingly, dry powder formulations is processed into particles having the appropriate mass median aerodynamic diameter (MMAD), tap density, and surface roughness to achieve delivery of the one or more active agents to the deep lung. Preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper-to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation, although very small particles may be exhaled.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodyanamic diameter for maximum deposition within the lungs can be calculated. See, for example, U.S. Pat. No. 7,052,678 to Vanbever, et al.

In some embodiments, the dry powder formulation is composed of a plurality of particles having a median mass aerodynamic diameter between about 0.5 to about 10 microns, more preferably between about 0.5 microns to about 7 microns, most preferably between about 0.5 to about 5 microns. In some embodiments, the dry powder formulation is composed of a plurality of particles having a median mass aerodynamic diameter between about 0.5 to about 3 microns. In some embodiments, the dry powder formulation is composed of a plurality of particles having a median mass aerodynamic diameter between about 3 to about 5 microns. In some embodiments, the dry powder formulation is composed of a plurality of particles having a median mass aerodynamic diameter between about 5 to about 7 microns. In some embodiments, the dry powder formulation is composed of a plurality of particles having a median mass aerodynamic diameter between about 7 to about 9.5 microns.

In some cases, there may be an advantage to delivering particles larger than about 3 microns in diameter. Phagocytosis of particles by alveolar macrophages diminishes precipitously as particle diameter increases beyond about 3 microns. Kawaguchi, H., et al., Biomaterials 7: 61-66 (1986); and Rudt, S. and Muller, R. H., J. Contr. Rel, 22: 263-272 (1992). By administering particles with an aerodynamic volume greater than 3 microns, phagocytic engulfment by alveolar macrophages and clearance from the lungs can be minimized.

In some embodiments, at least about 80%, more preferably at least about 90%, most preferably at least about 95% of the particles in dry powder formulation have aerodynamic diameter of less than about 10 microns, more preferably less than about 7 microns, most preferably about 5 microns. In some embodiments, at least about 80%, more preferably at least about 90%, most preferably at least about 95%, of the particles in dry powder formulation have aerodynamic diameter of greater than about 0.5 microns. In some embodiments, at least about 80%, more preferably at least about 90%, most preferably at least about 95%, of the particles in dry powder formulation have an aerodynamic diameter of greater than about 0.1 microns.

In some embodiments, at least about 80%, more preferably at least about 90%, most preferably at least about 95%, of the particles in dry powder formulation have aerodynamic diameter of greater than about 0.5 microns and less than about 10 microns, more preferably greater than about 0.5 microns and less than about 7 microns, most preferably greater than about 0.5 microns and less than about 5 microns. In some embodiments, at least about 80%, more preferably at least about 90%, most preferably at least about 95% of the particles in dry powder formulation have aerodynamic diameter of greater than about 0.5 microns and less than about 3 microns. In some embodiments, at least about 80%, more preferably at least about 90%, most preferably at least about 95% of the particles in dry powder formulation have aerodynamic diameter of greater than about 3 microns and less than about 5 microns. In some embodiments, at least about 80%, more preferably at least about 90%, most preferably at least about 95% of the particles in dry powder formulation have aerodynamic diameter of greater than about 5 microns and less than about 7 microns. In some embodiments, at least about 80%, more preferably at least about 90%, most preferably at least about 95% of the particles in dry powder formulation have aerodynamic diameter of greater than about 7 microns and less than about 9.5 microns.

In some embodiments, the particles have a tap density of less than about 0.4 g/cm$^3$, more preferably less than about 0.25 g/cm$^3$, most preferably less than about 0.1 g/cm$^3$. Features which can contribute to low tap density include irregular surface texture and porous structure.

In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulation s described below, and administered to the lung using methods known in the art for the delivery of liquid formulations.

2. Liquid Formulations

Liquid formulations contain one or more weight loss agents dissolved or suspended in a liquid pharmaceutical carrier.

Suitable liquid carriers include, but are not limited to distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human.

Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e., nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

3. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

Preferably, a dry powder or liquid formulation as described above is formulated into aerosol formulations using one or more propellants. Suitable propellants include air, hydrocarbons, such as pentane, isopentane, butane, isobutane, propane and ethane, carbon dioxide, chlorofluorocarbons, fluorocarbons, and combinations thereof. Suitable fluorocarbons include 1-6 hydrogen containing fluorocarbons, such as $CHF_2CHF_2$, $CF_3CH_2F$, $CH_2F_2CH_3$, and $CF_3CHFCF_3$ as well as fluorinated ethers such as $CF_3$—O—$CF_3$, $CF_2H$—O—$CHF_2$, and $CF_3$—$CF_2$—O—$CF_2$—$CH_3$. Suitable fluorocarbons also include perfluorocarbons, such as 1~4 carbon perfluorocarbons including $CF_3CF_3$, $CF_3CF_2CF_3$, and $CF_3CF_2CF_2CF_3$.

Preferably, the propellants include, but not limited to, one or more hydrofluoroalkanes (HFA). Suitable HFA propellants, include but are not limited to, 1,1,1,2,3,3,-heptafluoro-n-propane (HFA 227), 1,1,1,2-tetrafluoroethane (HFA 134) 1,1,1,2, 25 3,3,3-heptafluoropropane (Propellant 227), or any mixture of these propellants.

Preferably, the one or more propellants have sufficient vapor pressure to render them effective as propellants. Preferably, the one or more propellants are selected so that the density of the mixture is matched to the density of the particles in the aerosol formulation in order to minimize settling or creaming of the particles in the aerosol formulation.

The propellant is preferably present in an amount sufficient to propel a plurality of the selected doses of the aerosol formulation from an aerosol canister.

4. Devices for Pulmonary Administration

In some cases, a device is used to administer the formulations to the lungs. Suitable devices include, but are not limited to, dry powder inhalers, pressurized metered dose inhalers, nebulizers, and electrohydrodynamic aerosol devices.

Inhalation can occur through the nose and/or the mouth of the patient. Administration can occur by self-administration of the formulation while inhaling, or by administration of the formulation via a respirator to a patient on a respirator.

Dry Powder Inhalers

The dry powder formulations described above can be administered to the lungs of a patient using a dry powder inhaler (DPI). DPI devices typically use a mechanism such as a burst of gas to create a cloud of dry powder inside a container, which can then be inhaled by the patient.

In a dry powder inhaler, the dose to be administered is stored in the form of a non-pressurized dry powder and, on actuation of the inhaler, the particles of the powder are inhaled by the subject. In some cases, a compressed gas (i.e., propellant) may be used to dispense the powder, similar to pressurized metered dose inhalers (pMDIs). In some cases, the DPI may be breath actuated, meaning that an aerosol is created in precise response to inspiration. Typically, dry powder inhalers administer a dose of less than a few tens of milligrams per inhalation to avoid provocation of cough.

DPIs function via a variety of mechanical means to administer formulations to the lungs. In some DPIs, a doctor blade or shutter slides across the dry powder formulation contained in a reservoir, culling the formulation into a flowpath whereby the patient can inhale the powder in a single breath. In other DPIs, the dry powder formulation is packaged in a preformed dosage form, such as a blister, tabule, tablet, or gelcap, which is pierced, crushed, or otherwise unsealed to release the dry powder formulation into a flowpath for subsequent inhalation. Still others DPIs release the dry powder formulation into a chamber or capsule and use mechanical or electrical agitators to keep the dry powder formulation suspended in the air until the patient inhales.

Dry powder formulations may be packaged in various forms, such as a loose powder, cake, or pressed shape for insertion in to the reservoir of a DPI.

Examples suitable DPIs for the administration of the formulations described above include the Turbohaler® inhaler (Astrazeneca, Wilmington, Del.), the Clickhaler® inhaler (Innovata, Ruddington, Nottingham, UK), the Diskus® inhaler (Glaxo, Greenford, Middlesex, UK), the Easy-Haler®) (Orion, Expoo, FI), the Exubera® inhaler (Pfizer, New York, N.Y.), the Qdose® inhaler (Microdose, Monmouth Junction, N.J.), and the Spiros®) inhaler (Dura, San Diego, Calif.).

Pressurized Metered Dose Inhalers

The liquid formulations described above can be administered to the lungs of a patient using a pressurized metered dose inhaler (pMDI).

Pressurized Metered Dose Inhalers (pMDIs) generally include at least two components: a canister in which the liquid formulation is held under pressure in combination with one or more propellants, and a receptacle used to hold and actuate the canister. The canister may contain a single or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol.

pMDIs typically employ one or more propellants to pressurize the contents of the canister and to propel the liquid formulation out of the receptacle outlet, forming an aerosol. Any suitable propellants, including those discussed above, may be utilized. The propellant may take a variety of forms. For example, the propellant may be a compressed gas or a liquefied gas. Chlorofluorocarbons (CFC) were once commonly used as liquid propellants, but have now been banned. They have been replaced by the now widely accepted hydrofluororalkane (HFA) propellants.

pMDIs are available from a number of suppliers, including 3M Corporation, Aventis, Boehringer Ingleheim, Forest Laboratories, Glaxo-Wellcome, Schering Plough and Vectura. In some cases, the patient administers an aerosolized formulation by manually discharging the aerosolized formulation from the pMDI in coordination with inspiration. In this way, the aerosolized formulation is entrained within the inspiratory air flow and conveyed to the lungs.

In other cases, a breath-actuated trigger, such as that included in the Tempo® inhaler (MAP Pharmaceuticals, Mountain View, Calif.) may be employed that simultaneously discharges a dose of the formulation upon sensing inhalation. These devices, which discharge the aerosol formulation when the user begins to inhale, are known as breath-actuated pressurized metered dose inhalers (baMDIs).

Nebulizers

The liquid formulations described above can also be administered using a nebulizer. Nebulizers are liquid aerosol generators that convert the liquid formulation described able, usually aqueous-based compositions, into mists or clouds of small droplets, preferably having diameters less than 5 microns mass median aerodynamic diameter, which can be inhaled into the lower respiratory tract. This process is called atomization. The droplets carry the one or more active agents into the nose, upper airways or deep lungs when the aerosol cloud is inhaled. Any type of nebulizer may be used to administer the formulation to a patient, including, but not limited to pneumatic (jet) nebulizers and electromechanical nebulizers.

Pneumatic (jet) nebulizers use a pressurized gas supply as a driving force for atomization of the liquid formulation. Compressed gas is delivered through a nozzle or jet to create a low pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Examples of pneumatic nebulizers include, but are not limited to, PARI LC Plus®, PARI LC Sprint®, Devilbiss PulmoAide®), and Boehringer Ingelheim Respima®).

Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow moving aerosol stream which can be entrained in an inspiratory flow.

In some cases, the electromechanical nebulizer is an ultrasonic nebulizer, in which the liquid formulation is coupled to a vibrator oscillating at frequencies in the ultrasonic range. The coupling is achieved by placing the liquid in direct contact with the vibrator such as a plate or ring in a holding cup, or by placing large droplets on a solid vibrating projector (a horn). The vibrations generate circular standing films which break up into droplets at their edges to atomize the liquid formulation. Examples of ultrasonic nebulizers include DuroMist®, Drive Medical Beetle Neb®, Octive Tech Densylogic®, and John Bunn Nano-Sonic®.

In some cases, the electromechanical nebulizer is a mesh nebulizer, in which the liquid formulation is driven through a mesh or membrane with small holes ranging from 2 to 8 microns in diameter, to generate thin filaments which break up into small droplets. In certain designs, the liquid formulation is forced through the mesh by applying pressure with a solenoid piston driver (for example, the AERx® nebulizer), or by sandwiching the liquid between a piezoelectrically vibrated plate and the mesh, which results in a oscillatory pumping action (for example EFlow®), AerovectRx®), or TouchSpray® nebulizer). In other cases, the mesh vibrates back and forth through a standing column of the liquid to pump it through the holes. Examples of such nebulizers include the AeroNeb Go®, AeroNeb Pro®. PARI EFlow®, Omron 22UE®; and Aradigm AERx®.

Electrohydrodynamic Aerosol Devices

The liquid formulations described above can also be administered using an electrohydrodynamic (EHD) aerosol device. EHD aerosol devices use electrical energy to aerosolize liquid drug solutions or suspensions. Examples of EHD aerosol devices are known in the art. See, for example, U.S. Pat. No. 4,765,539 to Noakes et al. and U.S. Pat. No. 4,962,885 to Coffee, R.A.

The electrochemical properties of the formulation may be important parameters to optimize when delivering the liquid formulation to the lung with an EHD aerosol device and such optimization is routinely performed by one of skill in the art.

V. Methods of Treatment

Pharmaceutical formulations containing one or more of the weight loss agents described herein can be administered to induce weight loss in a pre-obese, obese, or morbidly obese patient, reduce body fat in a pre-obese, obese, or morbidly obese patient, reduce food intake in a pre-obese, obese, or morbidly obese patient, improve glucose homeostasis in a pre-obese, obese, or morbidly obese patient, prevent weight gain and/or prevent an increase in body mass index in a normal, pre-obese, obese, or morbidly obese patient, or combinations thereof.

In certain embodiments, the pharmaceutical formulations are administered to a patient suffering from obesity (e.g., a pro-obese, obese, or morbidly obese patient), an obesity-related disease or disorder, diabetes, insulin-resistance syndrome, lypodystrpohy, nonalcoholic steatohepatitis, a cardiovascular disease, polycystic ovary syndrome, or a metabolic syndrome.

In cases where the pharmaceutical formulations are administered to normalize blood sugar, the formulations are preferably administered in an amount effective to lower blood glucose levels to less than about 180 mg/dL. The formulations can be co-administered with other anti-diabetic therapies, if necessary, to improve glucose homeostasis.

Pharmaceutical formulations may also be administered to patients suffering from a disease or disorder that causes obesity or predisposes a patient to become obese, such as Bardet-Biedl syndrome or a mutation in the gene encoding for the melanocortin receptor 4 (MC4R) protein (i.e., an MC4R mutation).

A. Dosages

The precise dosage administered to a patient will depend on many factors, including the physical characteristics of the patient (e.g., weight), the degree of severity of the disease or disorder to be treated, and the presence or absence of other complicating diseases or disorders and can be readily determined by the prescribing physician.

In certain embodiments, the weight loss agent is administered at a dosage equivalent to an oral dosage of between about 0.005 mg and about 500 mg per kg of body weight per day, more preferably between about 0.05 mg and about 100 mg per kg of body weight per day, most preferably between about 0.1 mg and about 10 mg per kg of body weight per day. In particular embodiments, the weight loss agent is administered at a dosage equivalent to an oral dosage of between about 1.0 mg and 5.0 mg per kg of body weight per day.

In some cases, a pharmaceutical formulation containing one or more of the weight loss agents is administered to a pre-obese, obese, or morbidly obese patient in a therapeutically effective amount to induce weight loss. In certain embodiments, a pharmaceutical formulation containing one or more of the weight loss agents is administered to a pre-obese, obese, or morbidly obese patient in a therapeutically effective amount to decrease body mass by at least 10%, more preferably by at least 15%, most preferably by at least 20%.

In some cases, a pharmaceutical formulation containing one or more of the weight loss agents is administered to a pre-obese, obese, or morbidly obese patient in a therapeutically effective amount to reduce body fat. In certain embodiments, a pharmaceutical formulation containing one or more of the weight loss agents is administered to a pre-obese, obese, or morbidly obese patient in a therapeutically effective amount to decrease body fat by at least 10%, more preferably by at least 15%, most preferably by at least 20%.

In some cases, a pharmaceutical formulation containing one or more of the weight loss agents is administered to a pre-obese, obese, or morbidly obese patient in a therapeutically effective amount to reduce food intake, appetite, or combinations thereof. In certain embodiments, a pharmaceutical formulation containing one or more of the weight loss agents is administered to a pre-obese, obese, or morbidly obese patient in a therapeutically effective amount to reduce average daily food intake (in terms of calories) by at least 15%, 17%, 20%, 22%, 25%, 28%, 30%, 32%, 35%, or greater.

In some cases, a pharmaceutical formulation containing one or more of the weight loss agents is administered to a pre-obese, obese, or morbidly obese patient in a therapeutically effective amount to improve glucose homeostasis. In certain embodiments, a pharmaceutical formulation containing one or more of the weight loss agents is administered to a pre-obese, obese, or morbidly obese patient in a therapeutically effective amount to reduce average fasting plasma blood glucose by at least 10%, 12%, 15%, 18%, 20%, 22%, 25%, or greater. In cases where the pharmaceutical formulations are administered to normalize blood sugar, the formulations are preferably administered in an amount effective to lower fasting plasma glucose levels to less than about 180 mg/dL, more preferably less than about 160 mg/dL, more preferably less than about 140 mg/dL.

B. Therapeutic Administration

Pharmaceutical formulations may be administered, for example, in a single dosage, as a continuous dosage, one or more times daily, or less frequently, such as once a week. The pharmaceutical formulations can be administered once a day or more than once a day, such as twice a day, three times a day, four times a day or more. In certain embodiments, the formulations are administered orally, once daily or less.

The pharmaceutical formulations are administered in an effective amount and for an effective period of time to elicit the desired therapeutic benefit. In certain embodiments, the pharmaceutical formulation is administered daily, bi-weekly, weekly, bi-monthly or monthly for a period of at least one week, two weeks, three weeks, four weeks, one month, two months, three months, four months, five months, six months, seven months, eight months, nine months, ten months, eleven months, one year, or longer.

The pharmaceutical formulations may also be administered prophylactically, e.g., to patients or subjects who are at risk for a disease or disorder such as diabetes or obesity. Thus, methods can also involve identifying a subject at risk for diabetes or obesity prior to administration of the formulations.

The exact amount of the formulations required will vary from subject to subject, depending on the species, age, sex, weight and general condition of the subject, extent of the disease in the subject, route of administration, whether other drugs are included in the regimen, and the like. Thus, it is not possible to specify an exact dosages for every formulation. However, an appropriate dosage can be determined by one of ordinary skill in the art using only routine experimentation. For example, effective dosages and schedules for administering the compositions may be determined empirically, and making such determinations is within the skill in the art.

Dosage can vary, and can be administered in one or more dose administrations daily, for one or several days. Guidance can be found in the literature for appropriate dosages for given classes of pharmaceutical products.

1. Co-Administration with Active Agents

In other embodiments, the compounds disclosed herein can be co-administered with one or more additional therapeutic, prophylactic, or diagnostic agents. Co-administration, as used herein, includes administration within the same dosage form or within different dosage forms. For those embodiments where the compounds described herein and the one or more additional therapeutic, prophylactic, or diagnostic agents are administered in different dosage forms, the dosage forms can be administered simultaneously (e.g., at the same time or essentially at the same time) or sequentially. "Essentially at the same time" as used herein generally means within ten minutes, preferably within five minutes, more preferably within two minutes, most preferably within in one minute. Dosage forms administered sequentially can be administered within several hours of each other, e.g., with ten hours, nine hours, eight hours, seven hours, six hours, five hours, four hours, three hours, two hours, one hour, 30 minutes, 20 minutes, or 15 minutes.

In certain embodiments, the weight loss agents described herein are co-administered with leptin or a leptin analog. In these cases, leptin or a leptin analog may be co-administered with the weight loss agents for a portion of the treatment period, or during the entirety of the treatment period. In preferred embodiments, the weight loss agents are co-administered with r-metHuLeptin (A-100, METRELEPTIN®), available from Amylin Pharmaceuticals (San Diego, Calif.).

In certain embodiments, the patients are suffering from diabetes. In these cases, the weight loss agents described herein may be co-administered with one or more therapies for diabetes.

Examples

Example 1: Administration of Celastrol to Obese Mice

Celastrol was obtained from commercial sources. C57B1/6J mice were placed on high fat diet (HFD; Research Diets, D12451, 45 kcal % fat) feeding for 16 weeks. After establishment of obesity and leptin resistance, mice were first administered celastrol at different doses (10, 50 and 100 µg/kg), in 25 µl DMSO, once per day) and vehicle (DMSO, 25 µl) by intraperitoneal (i.p.) injection. The animals had free access to food and water unless otherwise stated.

In all experiments, four days prior to drug administration, the animals went through an acclimation period where they were given saline (25 µl) to reduce the effect of stress created by i.p. injection. Following four days acclimation, celastrol was administered to HFD-fed obese mice daily by i.p. injection at increasing doses (10, 50 and 100 µg/kg) for three weeks in 25 µl of DMSO. A control group received the same volume of DMSO by i.p. injection.

Figure 1B:
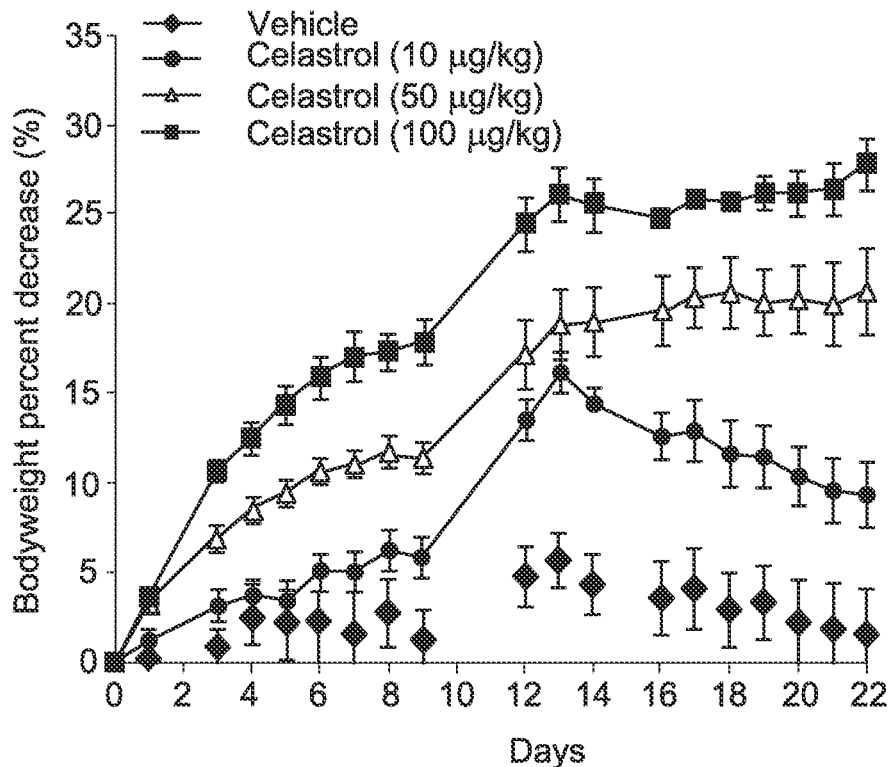
Figure 1C:
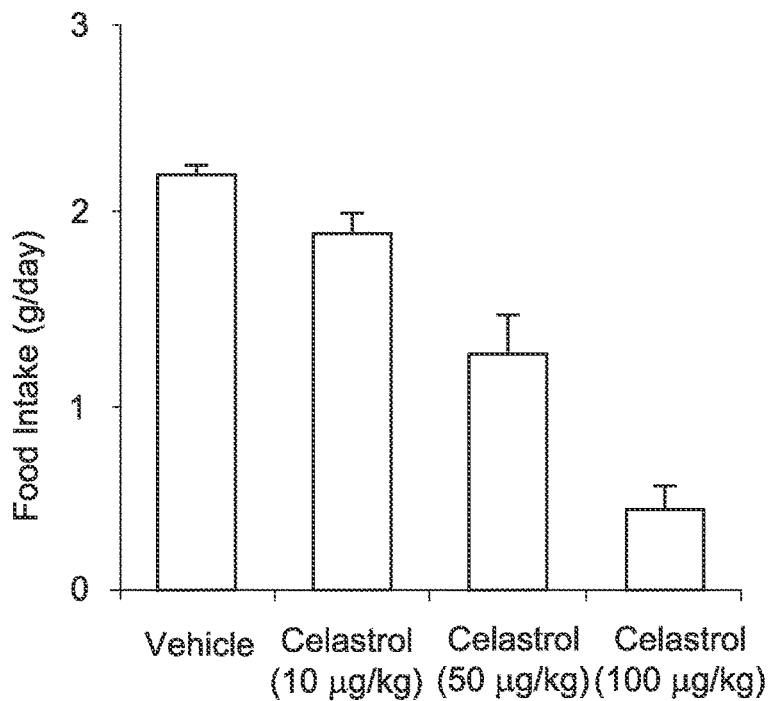
Figure 1D:
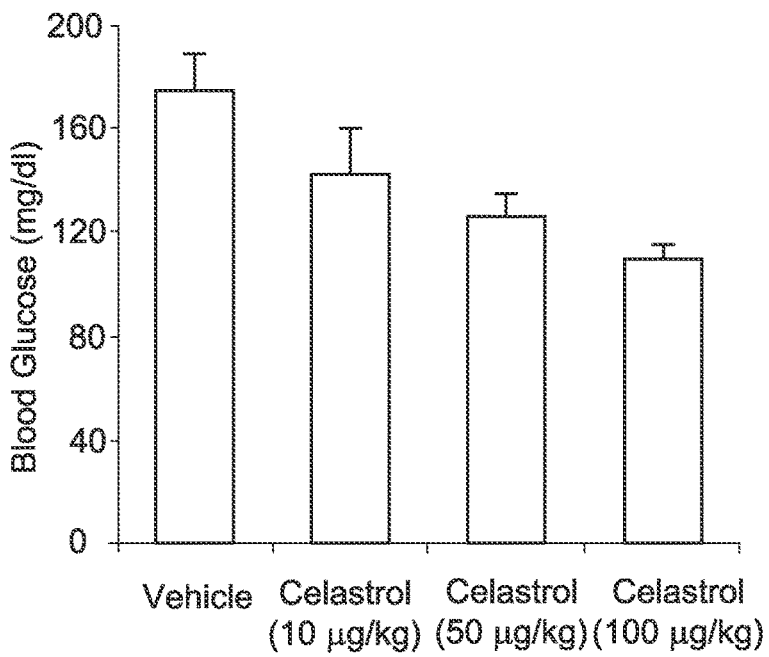

As shown in FIG. 1A, i.p. administration of celastrol significantly decreased the body weight (FIG. 1A, $p<0.001$, 100 µg/kg; FIG. 1B $p<0.05$, 10 µg/kg; $p<0.001$, 50 and 100 µg/kg) and food intake (FIG. 1C, $p<0.01$, three days average within the first week of drug administration) of HFD-fed obese mice in a dose dependent manner. At day 14 of the trial, we measured the 6-hour fasting blood glucose of mice. As shown in FIG. 1D, celastrol decreased the blood glucose of obese mice.

Example 2: Administration of Celastrol to Lean Mice

Figure 2A:
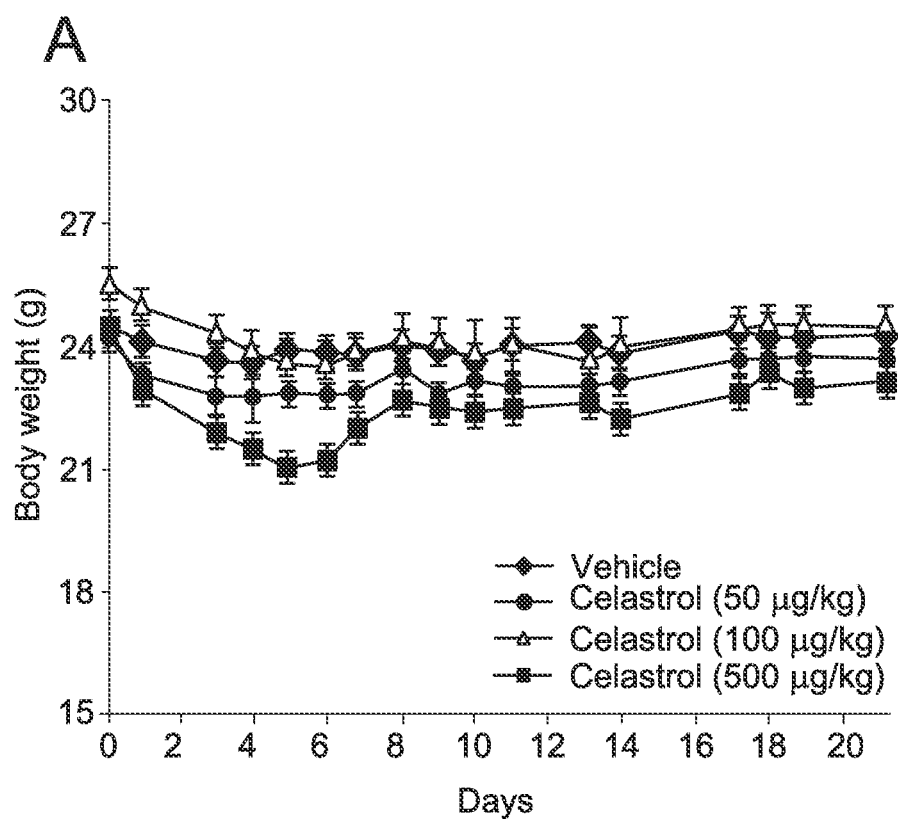
FIGS. 2A-2C illustrate the effect of celastrol, administered intraperitoneally (i.p.), on the food intake, body weight, and blood glucose levels of lean mice.
Figure 2B:
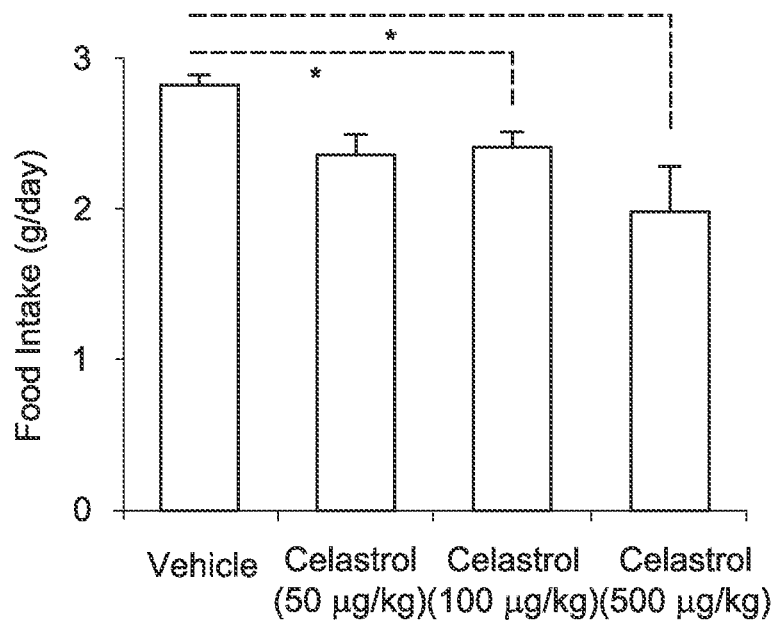
Figure 2C:
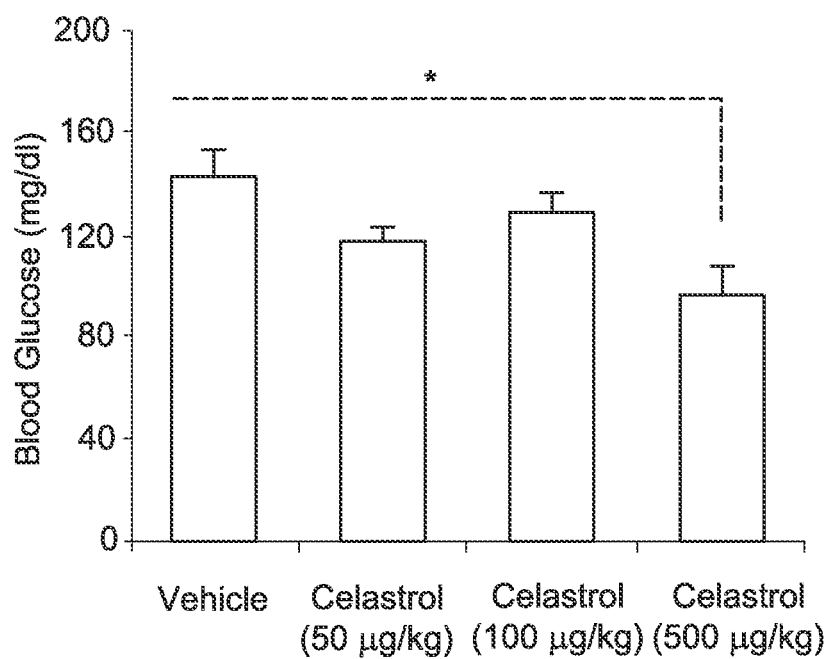

Celastrol was administered to lean mice on chow diet at 50, 100 or 500 µg/kg for three weeks by i.p. injections using the same protocol described above. As shown in FIG. 2A and FIG. 2B, celastrol induced a significant but small decrease in food intake; however, it did not induce bodyweight loss in lean mice, even when administered to lean mice at five times higher doses than effective to reduce body weight in obese mice. These findings suggest that the anorectic effect of celastrol is limited to obese animals. In lean mice, only the highest dose tested (500 µg/kg) induced a significant decrease in blood glucose (FIG. 2C, $p<0.05$) following 2 weeks of drug injections.

In combination, these findings suggest that celastrol can be administered in an effective amount (e.g., 100 µg/kg in these studies) to induce body weight loss in obese mice, but not in lean mice.

Example 3: Examination of the Leptin Dependence of Celastrol's Activity

Figure 3A:
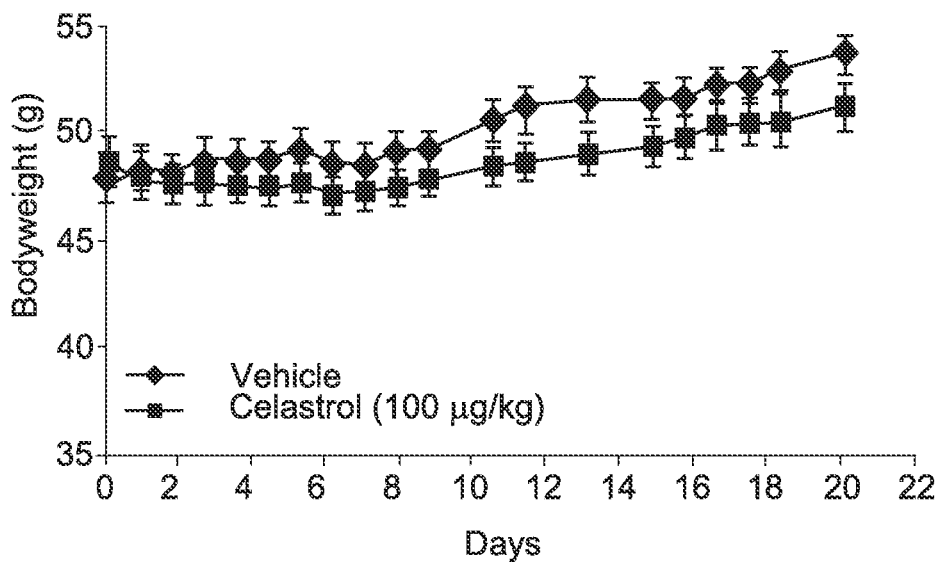
FIGS. 3A-3C illustrate the effect of celastrol, administered intraperitoneally (i.p.), on the food intake, body weight, and blood glucose levels of leptin deficient (ob/ob) mice.
Figure 3B:
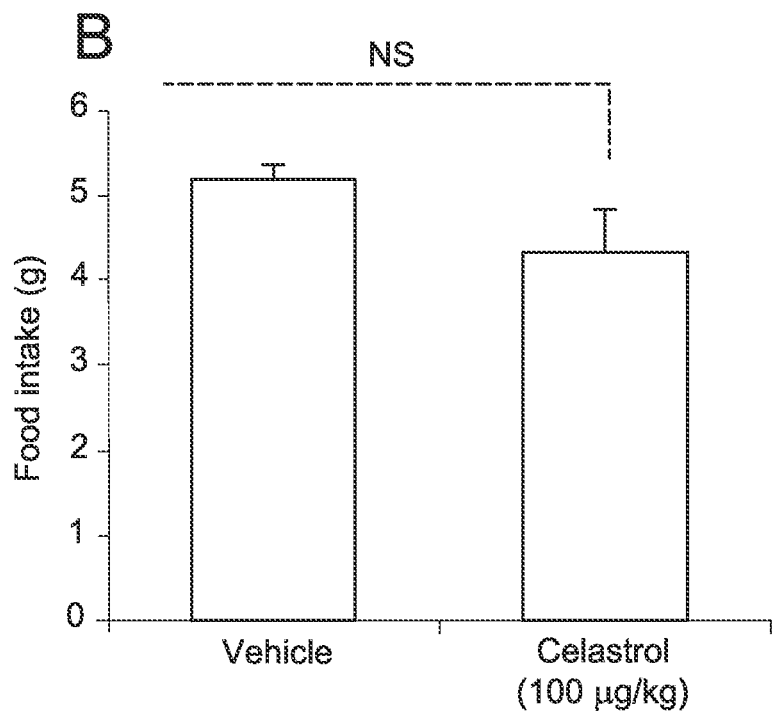
Figure 3C:
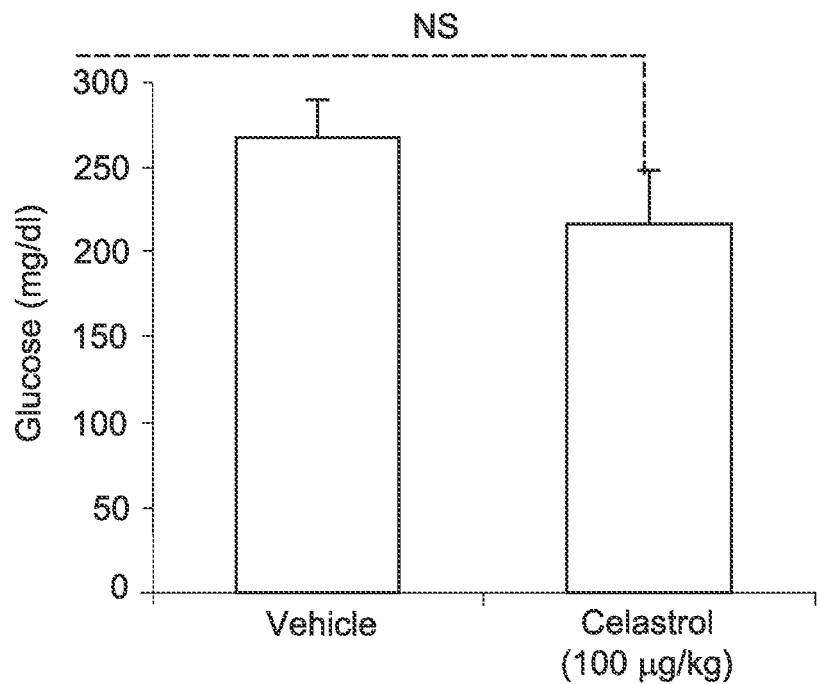
Figure 4A:
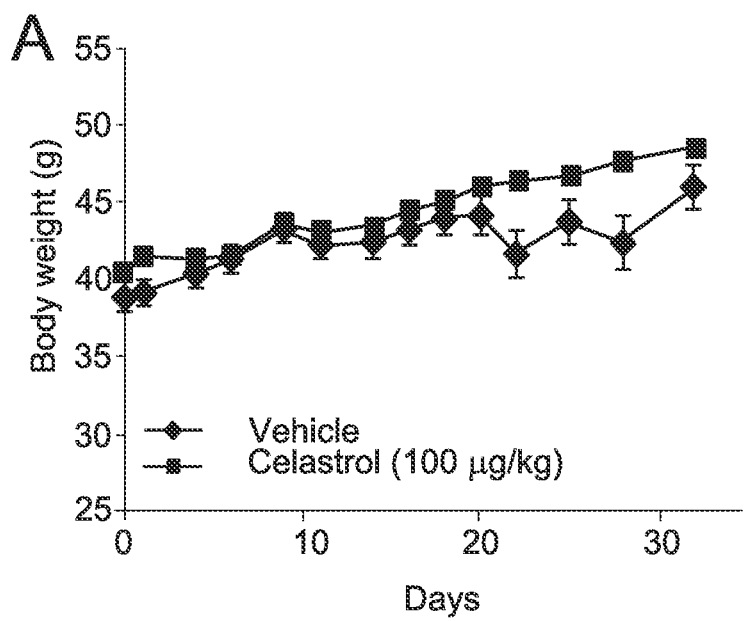
FIGS. 4A-4C illustrate the effect of celastrol, administered intraperitoneally (i.p.), on the food intake, body weight, and blood glucose levels of leptin receptor deficient (db/db) mice.
Figure 4B:
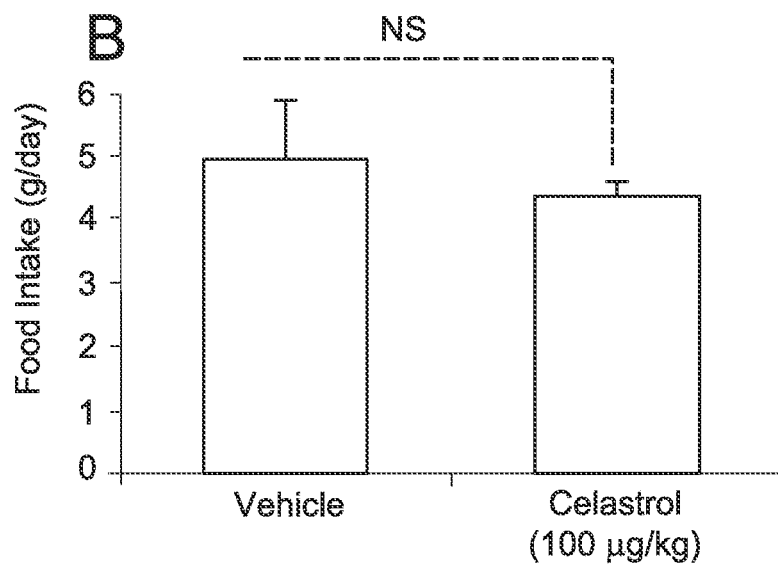
Figure 4C:
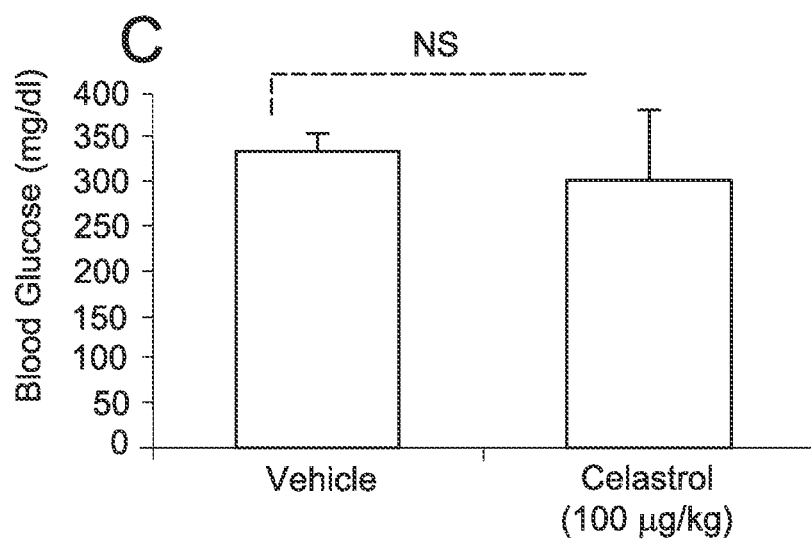

Celastrol (100 µg/kg, once a day, in 25 µl DMSO) was administered to leptin deficient (ob/ob) and leptin receptor deficient (db/db) mouse models of obesity. Neither of these mouse models showed a significant decrease in appetite upon celastrol administration (ob/ob mice, FIG. 3; db/db mice, FIG. 4). In both ob/ob and db/db mice, body weight continued to increase similar to the control (vehicle treated) group (ob/ob, FIG. 3A; db/db FIG. 4A). In addition, celastrol failed to decrease the 6-hour fasted blood glucose in either ob/ob (FIG. 3C), or db/db (FIG. 4C) mice after 2 weeks of drug injections.

Figure 5A:
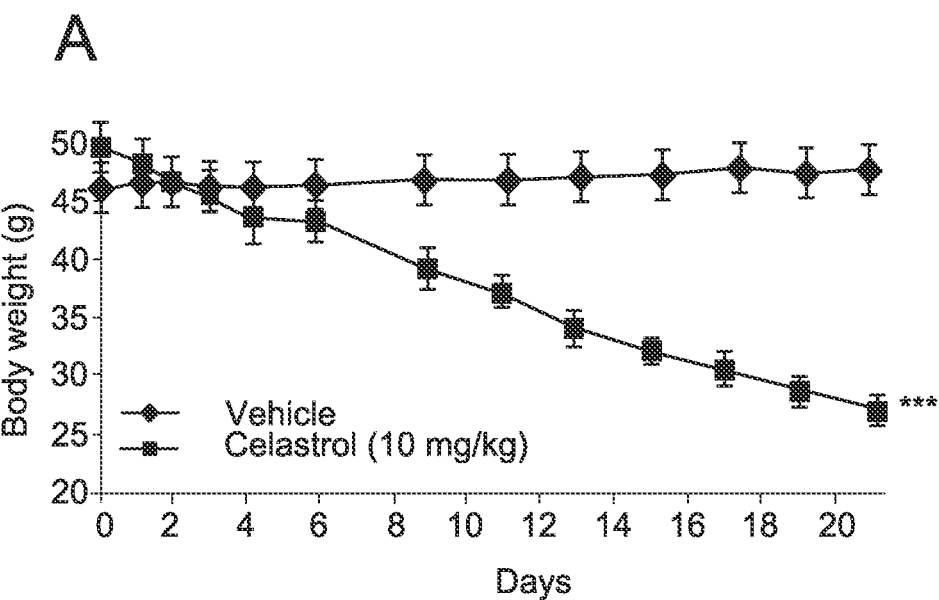
FIGS. 5A-5F illustrate the effect of celastrol, administered orally, on the food intake, body weight, and blood glucose levels of HFD-fed obese mice.
Figure 5B:
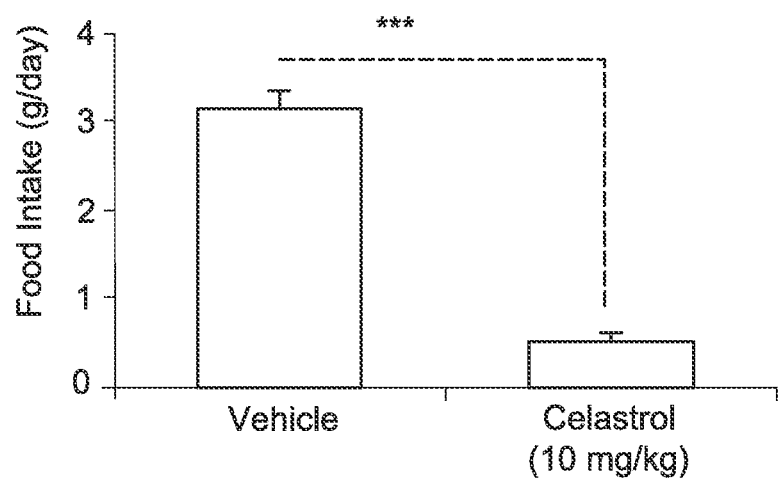
Figure 5C:
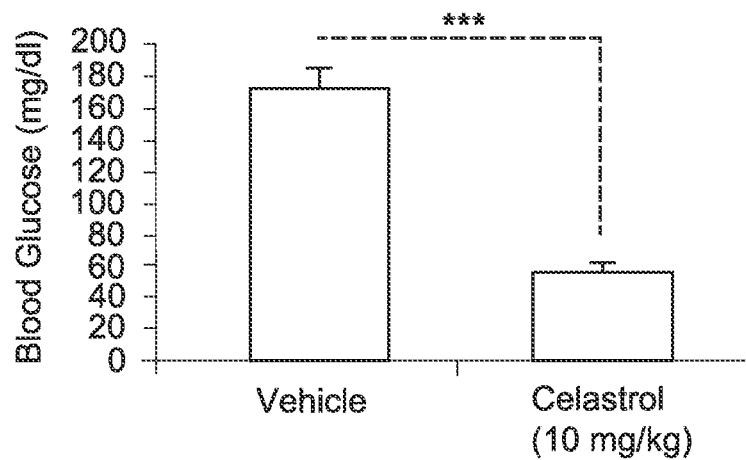
Figure 5D:
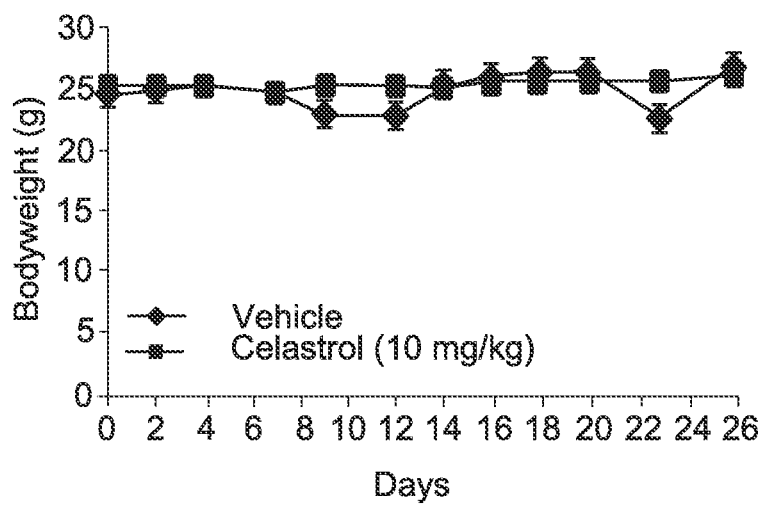
Figure 5E:
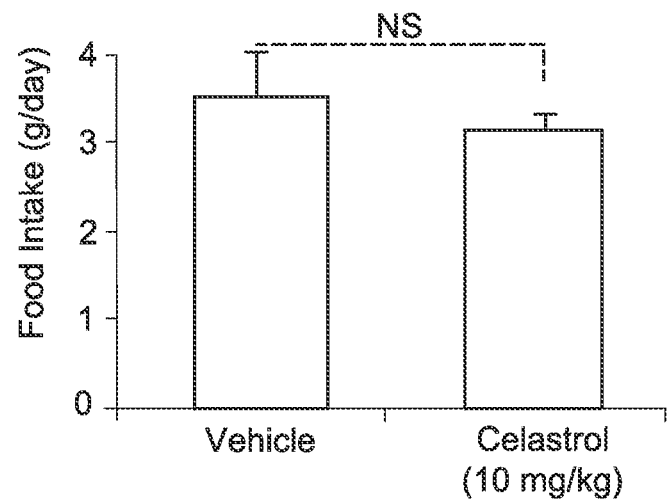
Figure 5F:
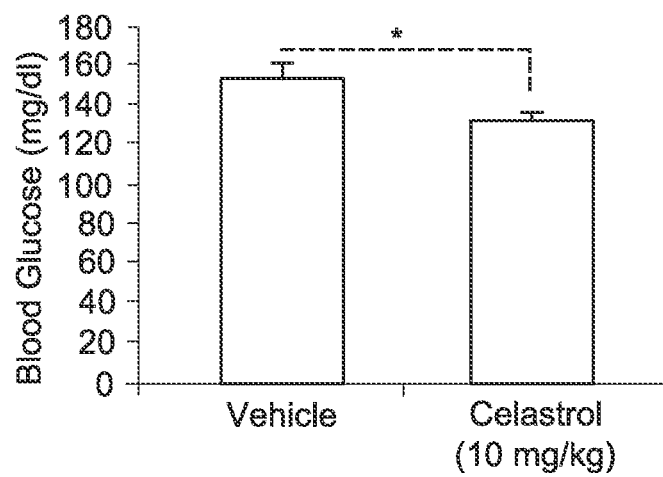
Figure 6A:
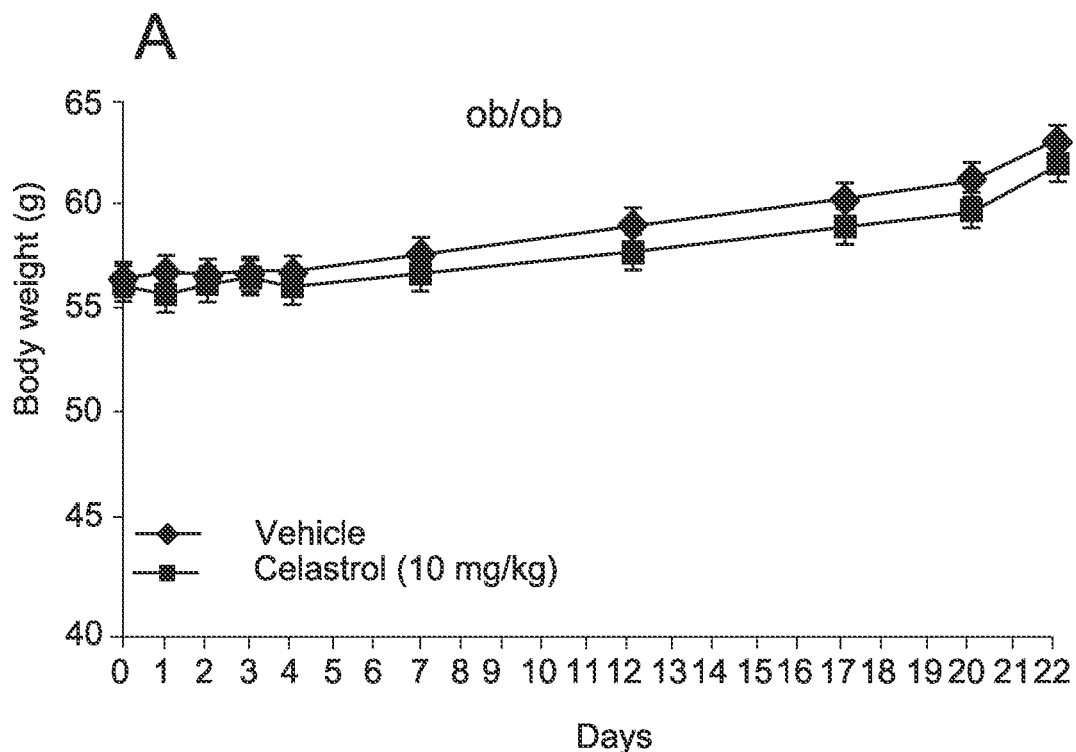
FIGS. 6A-6D illustrate the effect of celastrol, administered orally, on the food intake, body weight, and blood glucose levels of ob/ob and db/db mice.
Figure 6B:
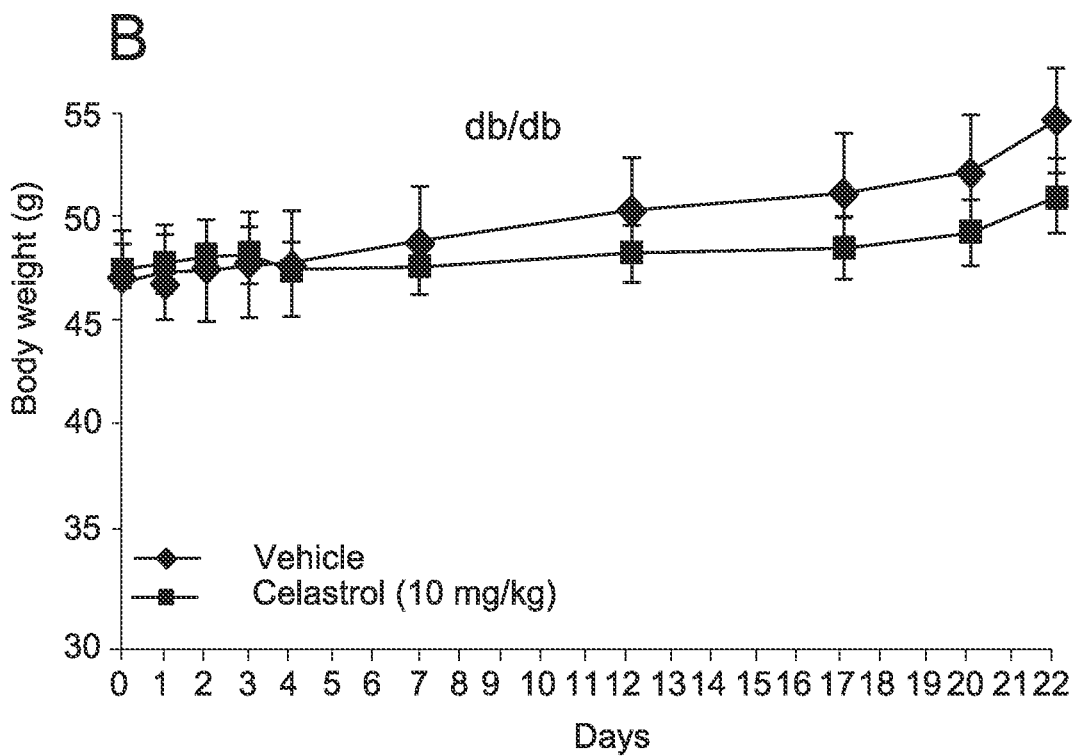
Figure 6C:
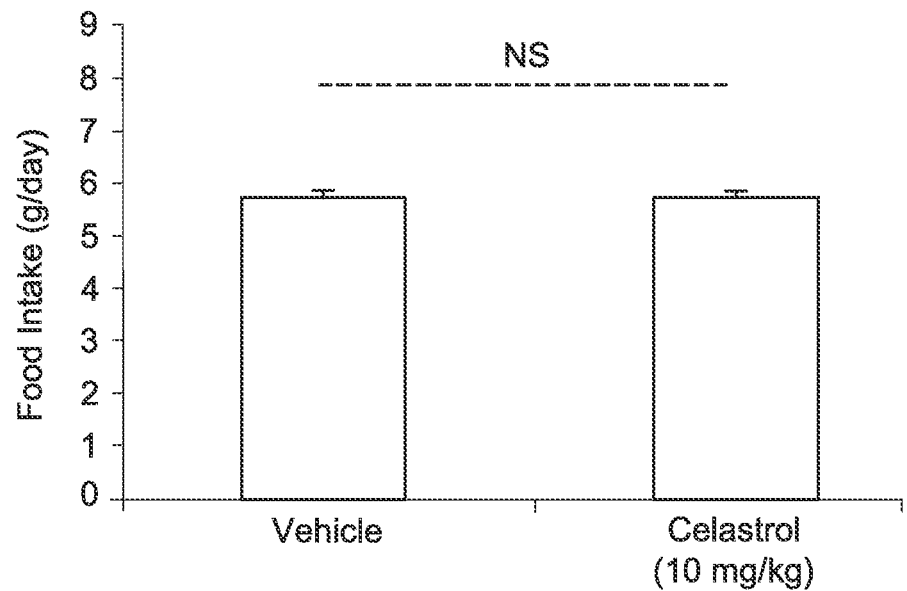
Figure 6D:
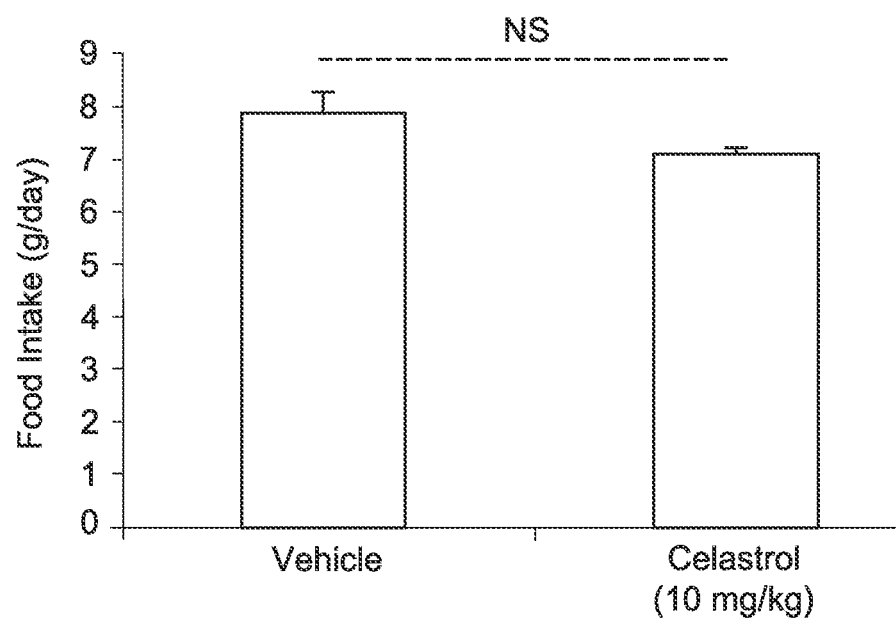

The ability of celastrol to exert anti-obesity effects when orally administered was also examined. Celastrol induced a robust and significant decrease in body weight (FIG. 5A, p<0.001), and food intake (FIG. 5B, p<0.001) in HFD-fed obese mice when administered orally at 10 mg/kg in a captisol suspension. In addition, oral celastrol decreased the 6-hour fasting blood glucose levels of HFD-fed obese mice (FIG. 5C, p<0.001, glucose reduced to hypoglycemic levels). However, no significant change in food intake (FIG. 5D) or body weight (FIG. 5E) was observed when lean mice were treated with celastrol orally. At this dose, oral celastrol administration resulted in a small but significant decrease in blood glucose levels of lean mice after three weeks of treatment (FIG. 5F). Moreover, ob/ob and db/db mice were completely unresponsive to oral celastrol treatment (FIG. 6A-D).

The fact that celastrol decreased body weight and food intake in HFD-fed obese mice but not in ob/ob or db/db mice suggests that anorectic effect of celastrol is mediated through leptin signaling. Although HFD-fed obese mice have elevated leptin levels, they develop leptin resistance and do not respond to exogenous leptin administration. It was therefore hypothesized that celastrol exerts anti-obesity effects through increasing leptin sensitivity in the brains of the HFD-fed obese mice. To test this hypothesis, leptin was administered to celastrol- or vehicle-treated HFD-fed obese animals. To avoid any possible leptin sensitizing effect of weight loss or decreased food intake created by celastrol administration, leptin injections were carried out upon acute celastrol treatment as described below.

Figure 7A:
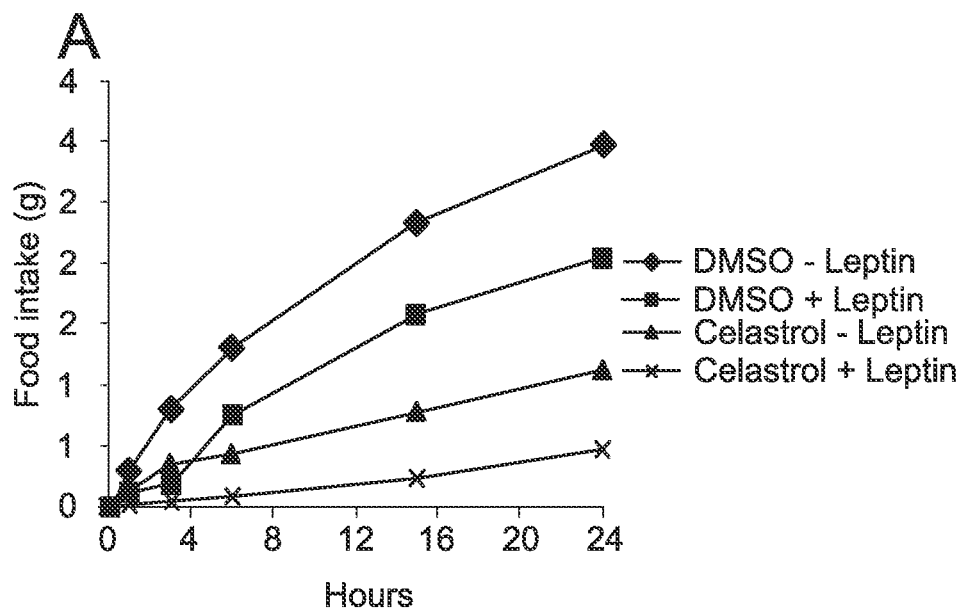
FIGS. 7A-7D illustrates the effect of co-administered leptin and celastrol on the bodyweight and food intake of mice.
Figure 7B:
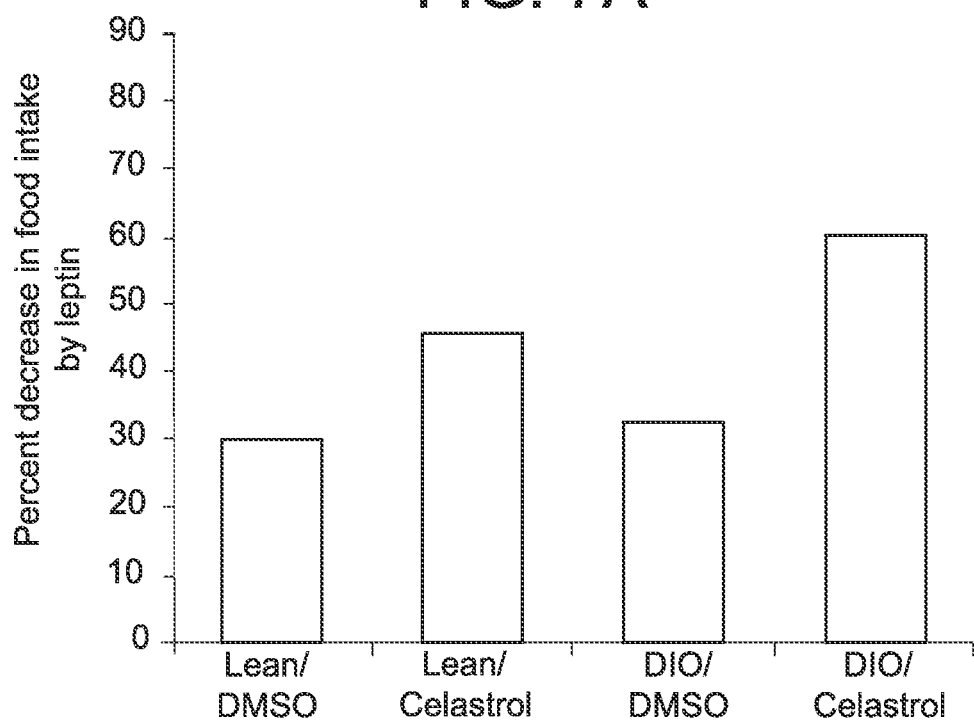
Figure 7C:
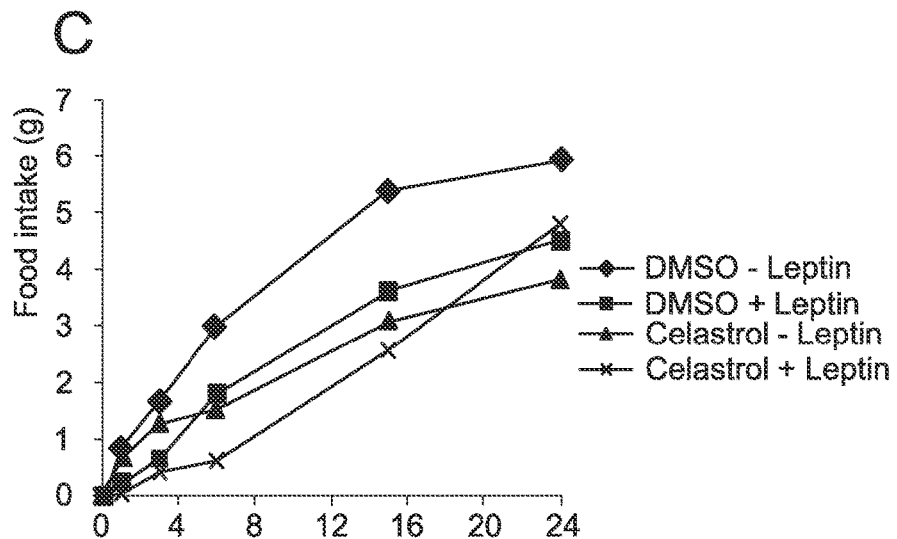
Figure 7D:
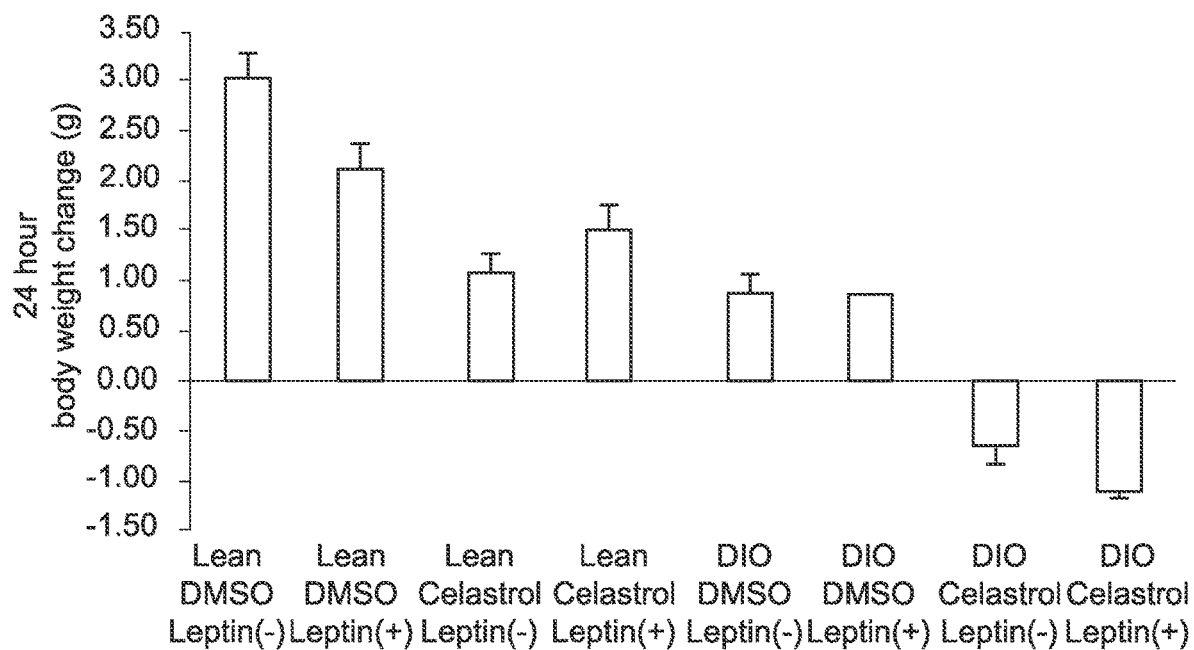

Lean and HFD-fed obese mice were divided into four groups: 1) DMSO+saline, 2) DMSO+leptin, 3) celastrol+saline, and 4) celastrol+leptin (n=3 per group). Mice were injected (ip) with 100 µg/kg celastrol or vehicle (DMSO) one hour before dark cycle (day zero). 24 hours later, mice were injected for a second time with celastrol or DMSO (day 1), and all animals were then taken to 24 hour-fasting. On day two, at 21 hours of fasting, mice received a final injection of DMSO or celastrol. 30 minutes prior to dark cycle, at 23.5 hour of fasting, mice received a single ip injection of leptin (10 mg/kg, dissolved in saline), or saline. 30 minutes later (end of 24-hour fasting) mice were provided with their previous diet (either regular chow or HFD) ad libitum. 1, 3, 6, 15, and 24-hour food intake and 24-hour body weight changes were recorded (FIG. 7A). At the 6-hour time point, leptin reduced food intake by approximately 40% in DMSO-treated lean and HFD-fed obese groups. Celastrol treated lean mice showed a 60% decrease in food intake upon leptin injection, whereas HFD-fed mice exhibited an 80% decrease in food intake upon leptin injection (FIG. 7B). During the 24 hour ad libitum feeding period all lean mice and vehicle-treated HFD-fed obese mice gained weight, whereas celastrol treated HFD-fed obese mice continued to exhibit weight loss. This weight loss was further increased (approximately two fold) by leptin administration (FIG. 7D). This is clearly evident when food intake of the celastrol-treated mice is calculated in percent values (FIG. 7B). In addition, HFD-fed obese mice were resistant to the weight reducing effect of leptin unless they received celastrol (FIG. 7D). Of note, celastrol alone, as expected, decreased the weight gain of HFD-fed obese mice in the absence of exogenous leptin administration, probably due to already elevated leptin levels of HFD-fed obese mice.

Figure 8A:
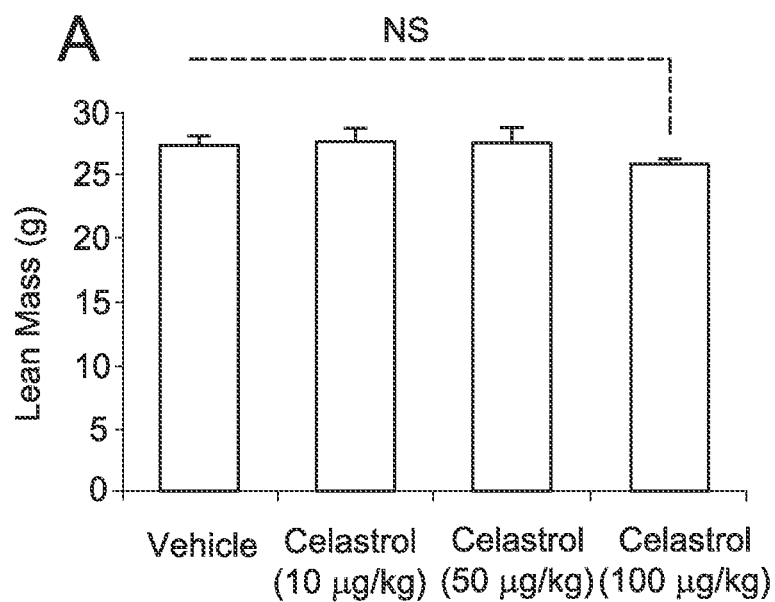
FIGS. 8A-8D illustrate the ability of celastrol to selectively decrease the fat mass (i.e., body fat) of HFD-fed mice.
Figure 8B:
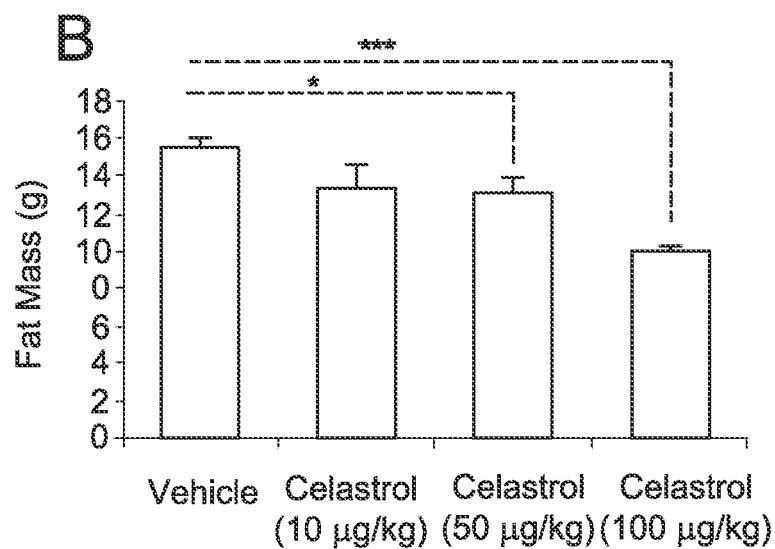
Figure 8C:
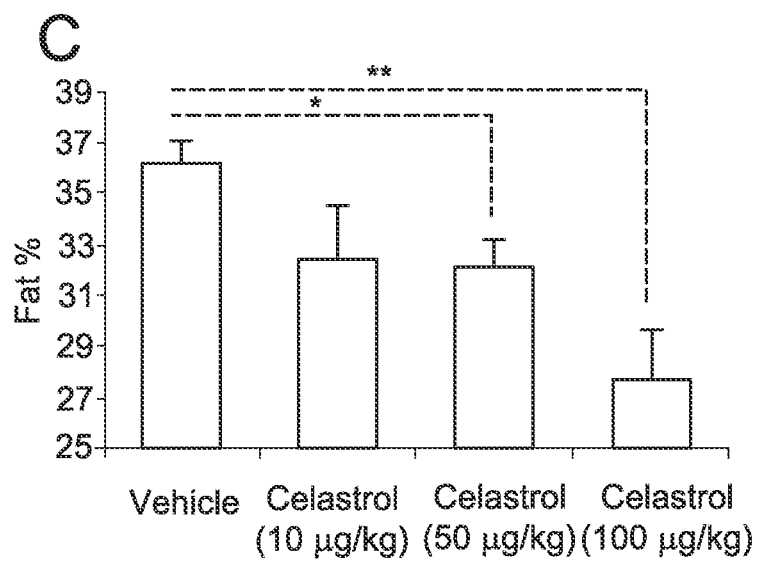
Figure 8D:
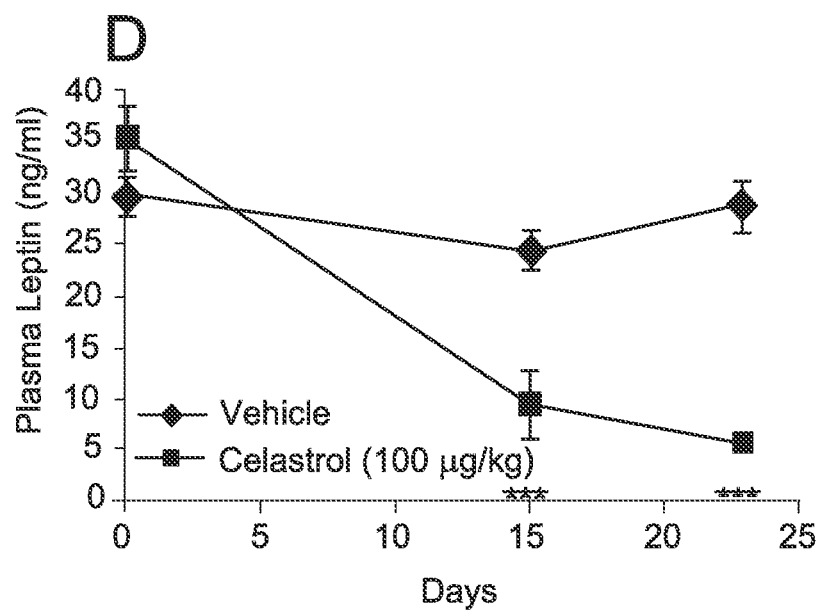

To analyze the change in body composition during celastrol treatment (ip 100 µg/kg), the lean mass and fat mass of mice was measured using Dual-Emission X-ray Absorptiometry (DEXA). Lean mass remained unchanged after two weeks of chronic celastrol administration (FIG. 8A). This is consistent with celastrol not having a toxic effect causing anorexia, since lean mass was preserved. However, fat mass and fat percentage was decreased significantly in celastrol-treated HFD-fed animals (FIGS. 8B-8C). Consistent with decreased adipose mass, leptin levels were shown to decrease gradually during chronic celastrol administration (FIG. 8D). In addition, food intake of HFD-fed obese mice gradually rose towards the end of the study as the endogenous leptin levels decrease. This finding supports the hypothesis that anorexic effect of celastrol is dependent on leptin signaling.

Locomotor activity was also normal in celastrol-treated mice. This is consistent with celastrol not having a toxic effect causing anorexia and weight loss, since the latter would be associated with decreased locomotor activity.

Example 4: Effect of Celastrol Administration on Glucose Homeostasis

As described above, i.p. and oral administration of celastrol results in a robust decrease in blood glucose levels in HFD-fed obese mice. In order to analyze the effect of celastrol on glucose homeostasis, Glucose Tolerance Tests (GTT) and Insulin Tolerance Tests (ITT) were performed following chronic i.p. celastrol administration (100 µg/kg).

For the GTT, mice were fasted overnight following one week of celastrol treatment and received an i.p. injection of D-glucose (0.75 g/kg) in the morning. For ITT, after 16 days of celastrol treatment, mice were fasted for 6 hours (from 8 a.m. to 2 p.m.) and recombinant human insulin (1 IU/kg from Eli Lilly) was injected intraperitoneally. In both procedures, blood glucose was measured from tail vein blood at 0, 15, 30, 60, 90 and 120 minutes following injection.

Figure 9A:
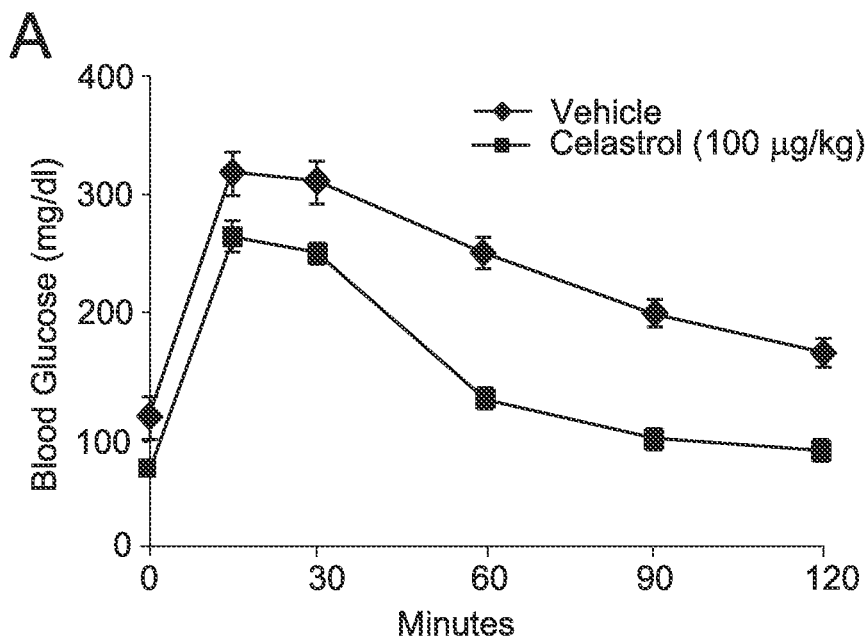
FIGS. 9A-9D illustrate the effect of celastrol on glucose homeostasis in HFD-fed obese mice.
Figure 9B:
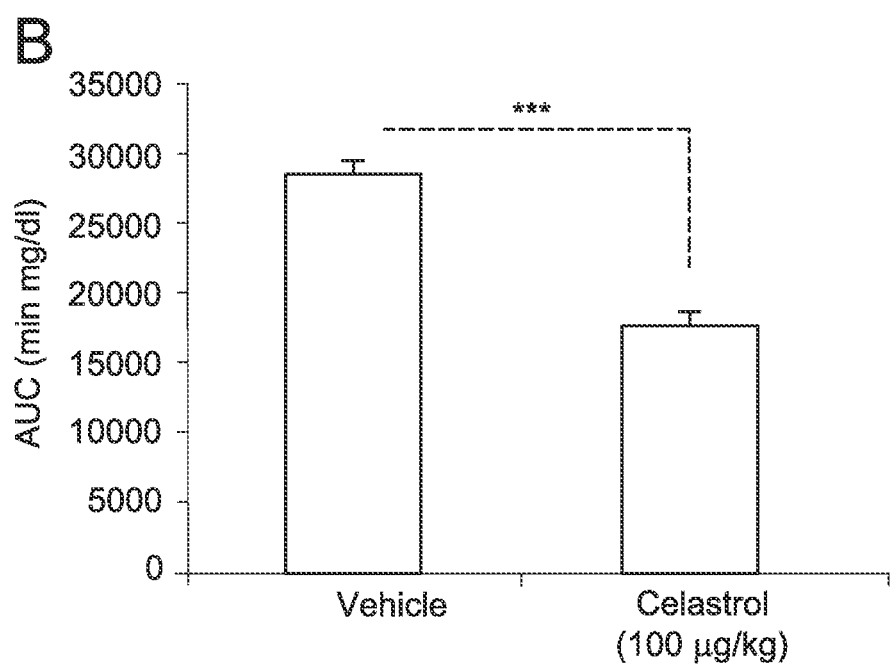
Figure 9C:
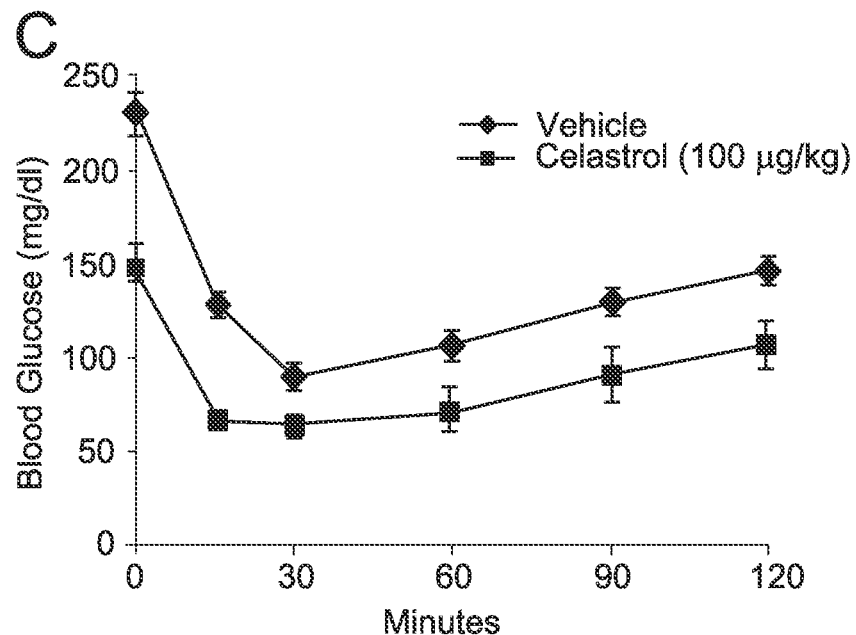
Figure 9D:
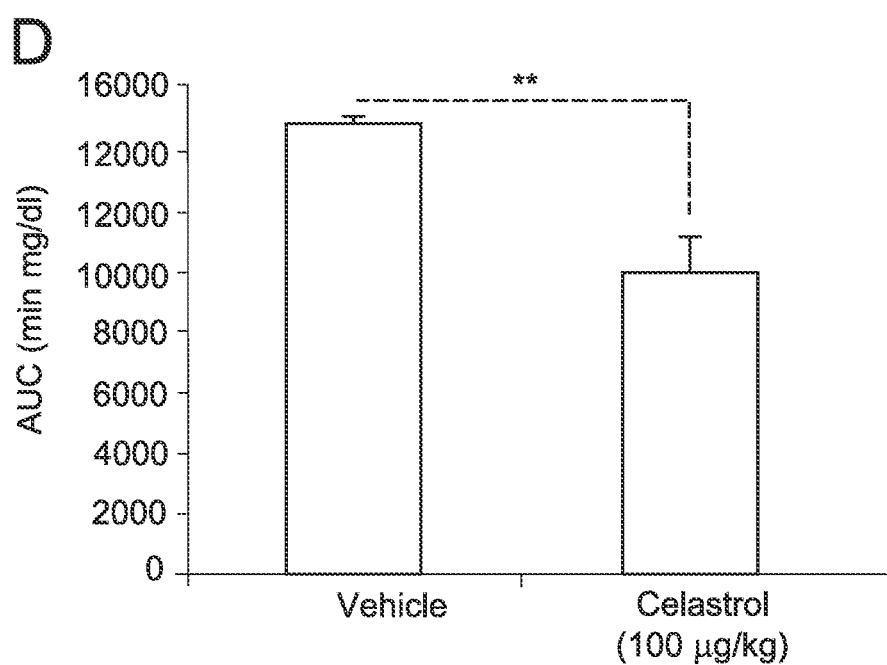
Figure 10A:
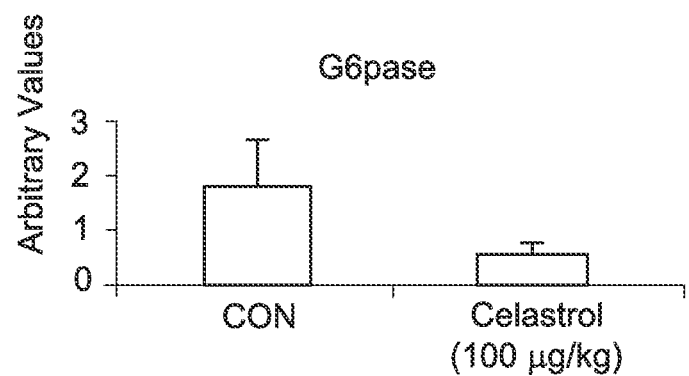
FIGS. 10A-10C illustrate the effect of celastrol administration on the hepatic mRNA expression of gluconeogenic enzymes in HFD-fed obese mice, as determined by quantitative PCR at the end of a 3-week i.p. administration of celastrol (100 µg/kg celastrol by i.p. once a day).
Figure 10B:
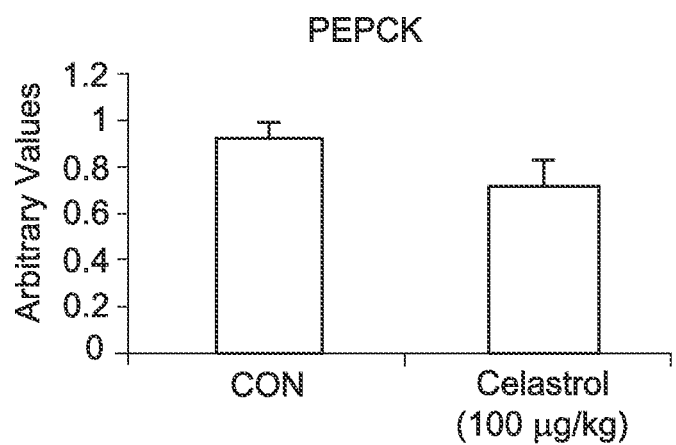
Figure 10C:
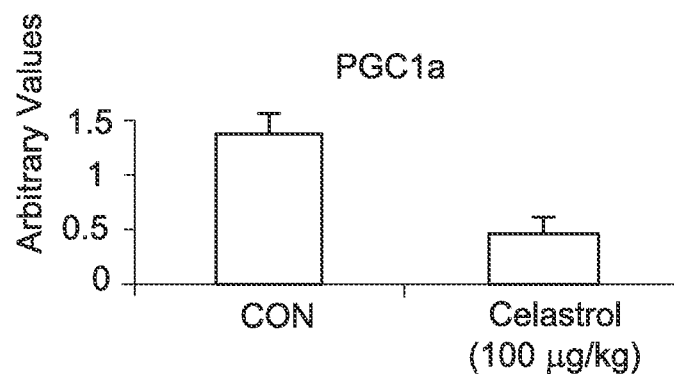

As shown in FIG. 9A, after one week of celastrol treatment, glucose homeostasis significantly improved in celastrol-treated mice when compared with the vehicle-treated mice, as evidenced by the difference in Area Under the Curve (AUC) of GTT (FIG. 9B, p<0.001). At day 16, ITT was performed. HFD-fed obese mice also exhibited improved insulin sensitivity (FIGS. 9C-9D, p<0.01). Consistent with improved glucose homeostasis, celastrol treated mice exhibited decreased hepatic mRNA expression of the gluconeogenic enzymes Phosphoenolpyruvate carboxykinase (PEPCK), Glucose 6-phosphatase (G6Pase) and Peroxisome proliferator-activated receptor gamma coactivator 1-alpha (PGC1a) (FIG. 10).

Example 5: Effect of Celastrol Administration on Liver, Kidney, and Thyroid Function To investigate the effect of celastrol administration on liver function, serum levels of alanine transaminase (ALT) and aspartate transaminase (AST) were measured in mice following three weeks of celastrol treatment (100 µg/kg, i.p.). ALT and AST were measured using an enzyme-linked immunosorbent assay (ELISA) kit (from Bio Scientific).

Figure 11A:
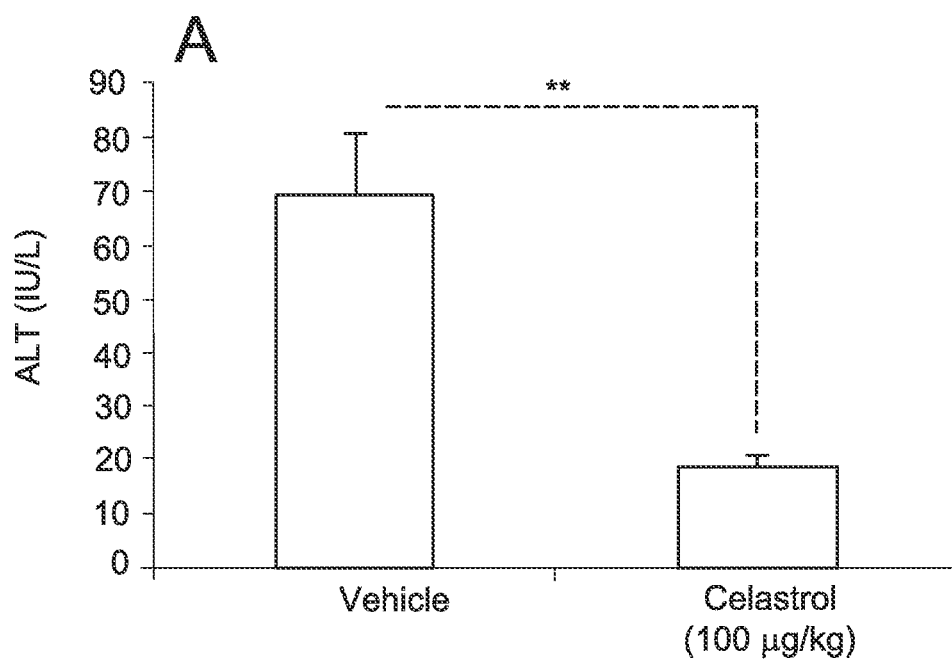
FIGS. 11A-11B illustrate the effect of celastrol administration on the serum levels of alanine transaminase (ALT) and aspartate transaminase (AST) in HFD-fed obese mice, as determined by ELISA, at the end of a 3-week i.p. administration of celastrol (100 µg/kg celastrol by i.p. once a day).
Figure 11B:
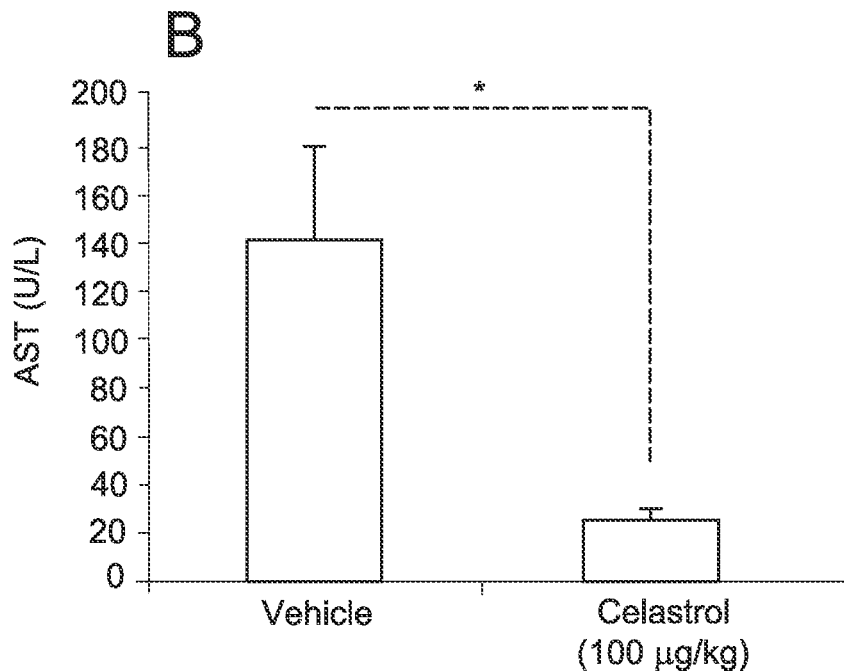

As shown in FIG. 11, celastrol administration decreases ALT and AST levels of HFD-fed obese mice, suggesting improved liver function. This finding was further confirmed histologically. Liver tissue harvested from these mice was fixed overnight in formalin, sectioned, and Hematoxylin and Eosin (H&E) stained. Hepatosteatosis in HFD-fed obese animals was reduced by celastrol treatment. Liver sections obtained from celastrol-treated mice appear virtually identical to the livers of lean mice. Similarly, there was no detectable change in kidney morphology of these mice. These results indicate that celastrol treatment also reduces hepatosteatosis.

Thyroid hormones are known to increase basal metabolic rate and hence increase energy expenditure. Elevated levels of thyroid hormones are known to decrease bodyweight with various undesired side effects. To examine if thyroid hormones may play a role in the anorectic action of celastrol, the plasma T3 and T4 levels of HFD-fed obese mice were measured after 3 weeks of celastrol treatment (100 μg/kg, i.p.). Thyroid hormones, including T3 and T4, are known to be elevated in HFD-fed obese animals.

Figure 12A:
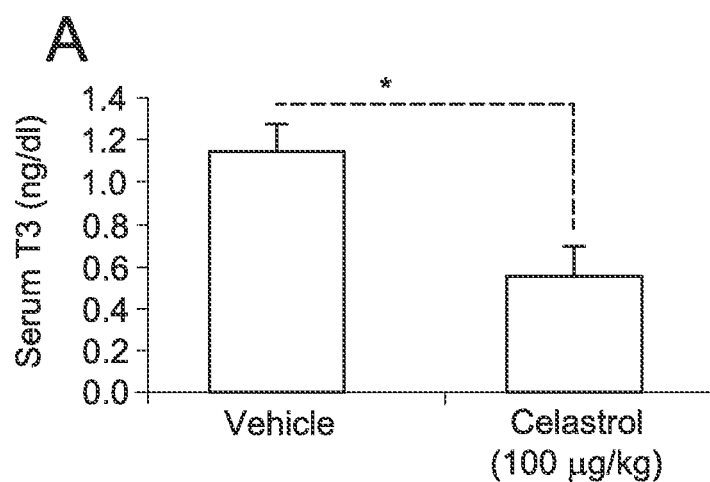
FIGS. 12A-12B illustrate the effect of celastrol administration on the serum levels of thyroid hormones triiodothyronine (T3) and thyroxine (T4) in HFD-fed obese mice at the end of a 3-week i.p. administration of celastrol (100 μg/kg celastrol by i.p. once a day).
Figure 12B:
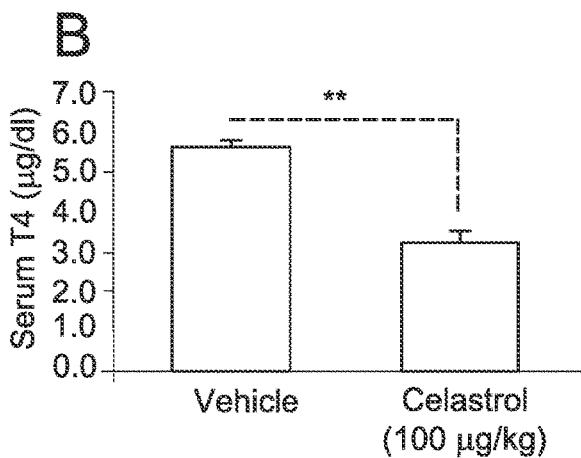

As shown in FIG. 12, celastrol decreases T3 and T4 levels in HFD-fed obese mice. This decrease is likely a consequence of weight loss, and suggests that the weight reducing effect of celastrol is not mediated by increased thyroid hormone activity.

Example 6: Preparation and Activity of Celastrol Derivatives

Celastrol is a Michael acceptor, and can form Michael adducts with nucleophiles, such as the cysteine residues of proteins. Four derivatives (mCS1-mCS4) of celastrol were prepared containing a substituent blocking the formation of Michael adducts at the reactive position of celastrol (the $C^6$-carbon atom of Formula I). These derivatives would no longer be expected to function as Michael acceptors.

Preparation of mCS1

20 mg (0.0378 mmol) celastrol was dissolved in 1 mL ethanol at room temperature. 50 μL 2-mercaptothanol was added, and the reaction was stirred for 30 min at room temperature. During the reaction time, the color of the reaction mixture changed from bright orange to colorless. Complete consumption of the starting material was confirmed by LC/MS. The solvent was then removed under reduced pressure to yield mCS1m1 in quantitative yield as faint orange film. Further purification can be performed on silica gel.

Preparation of mCS2

10 mg (0.0189 mmol) celastrol was dissolved in 1 mL ethanol at room temperature. 3 mg cystamine was added, and the reaction was stirred. A color change from bright orange to almost colorless was observed within 10 min. Following stirring over night at room temperature, mCS2 was precipitated, isolated by filtration, and dried under reduced pressure.

Preparation of mCS3

10 mg (0.0189 mmol) celastrol was dissolved in 1 mL ethanol at room temperature. 5 μL 3-mercaptopropionic acid was added, and the reaction was stirred. A color change from bright orange to almost colorless was observed within 1 hr stirring at room temperature. The solvent was removed under reduced pressure to yield mCS3 in quantitative yield as faint orange film.

Preparation of mCS4

10 mg (0.0189 mmol) celastrol was dissolved in 1 mL ethanol at room temperature. 5 mg D-cysteine was added, and the reaction was stirred at room temperature. A color change from bright orange to almost colorless was observed within 1 hr stirring at room temperature. The solvent was removed under reduced pressure to yield mCS4 in quantitative yield as an off-white solid.

Activity of mCS1-mCS4

Figure 13:
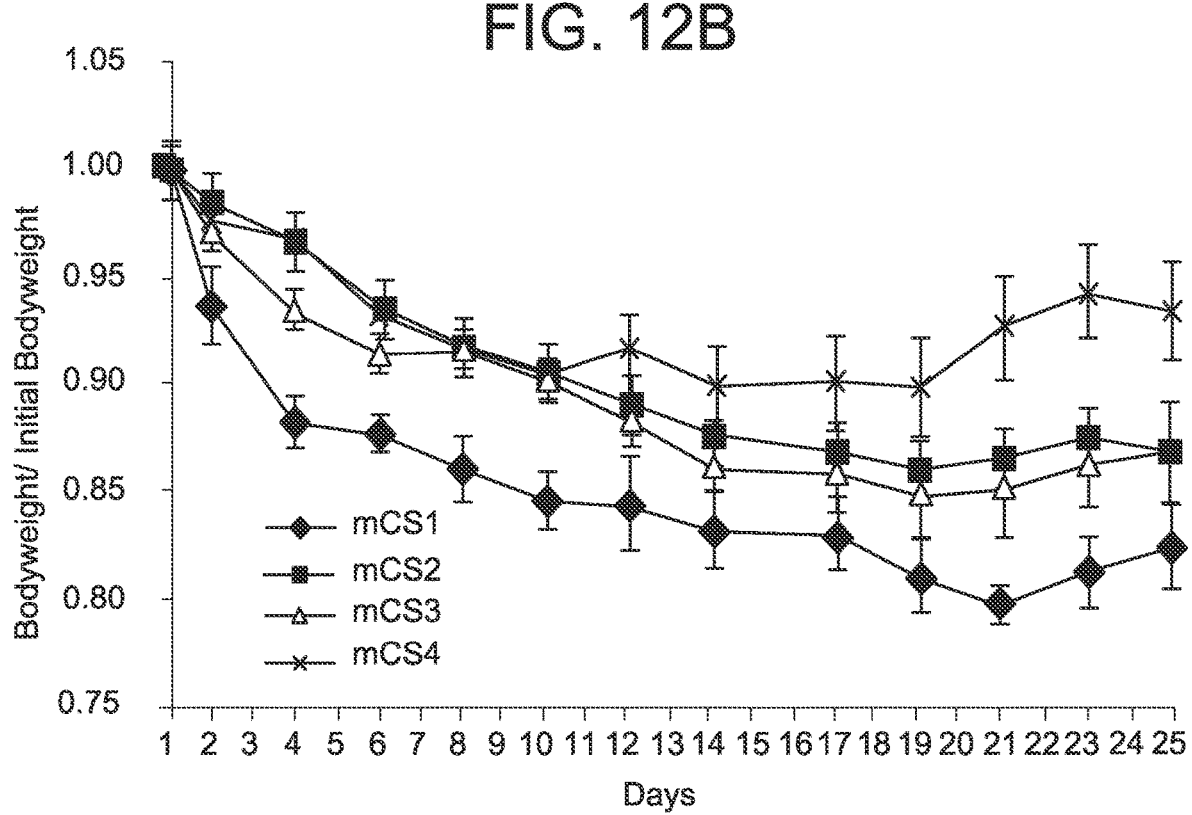
FIG. 13 is a graph plotting the bodyweight/initial bodyweight of HFD-fed obese mice as a function of time (days) for treatment with four different celastrol derivatives administered at a dose of 100 μg/kg by i.p. once a day (mCS1 (diamond trace), mCS2 (square trace), mCS3 (triangle trace), and mCS4 (cross trace)).

The four celastrol derivatives (mCS1-mCS4) were administered to HFD-fed obese mice (100 μg/kg/day for 25 days, i.p.). As shown in FIG. 13, mCS1-mCS4 decreased body weight and food intake with a similar potency to celastrol.

Example 7: Co-Administration of Celastrol and Leptin

Celastrol and leptin were co-administered to decrease the bodyweight of obese mice. C57B1/6J mice were placed on a high fat diet feeding for 16 weeks. Subsequently, celastrol was administered (100 μg/kg/day, i.p.) for a period of 40 days.

Figure 14:
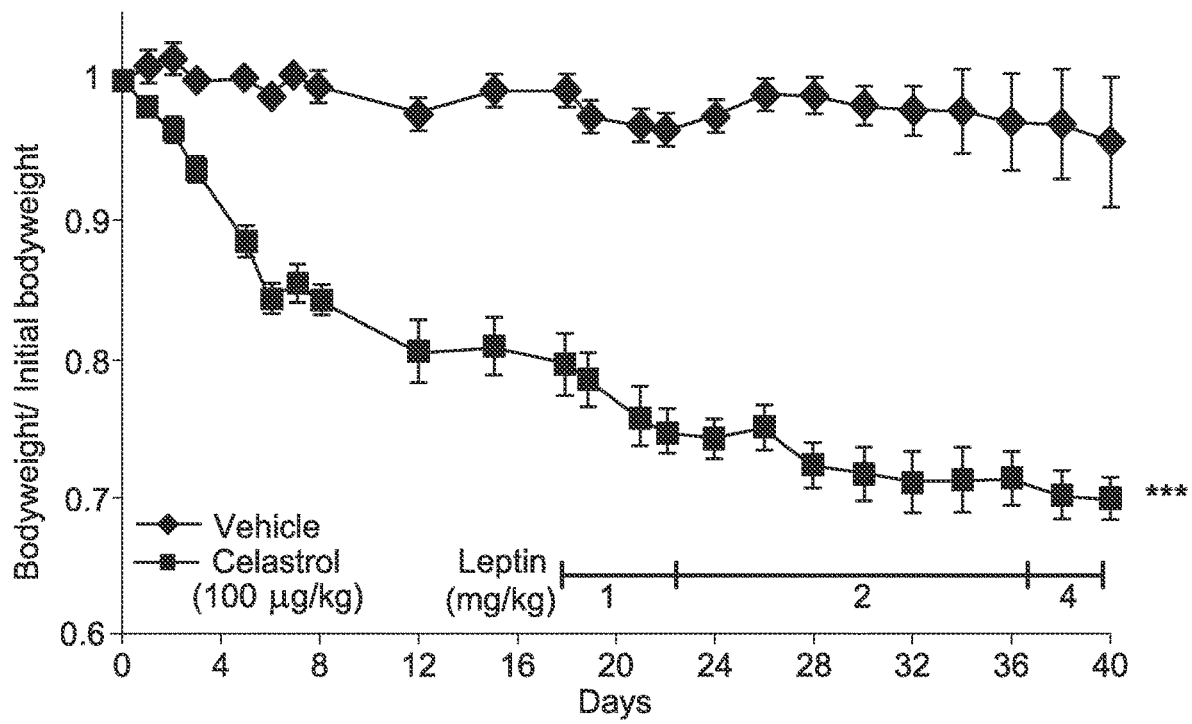
FIG. 14 is a graph plotting the bodyweight/initial bodyweight of HFD-fed obese mice as a function of time (days) for treatment with celastrol (vehicle control (diamond trace), 100 μg/kg celastrol by i.p. once a day (square trace)). Leptin was co-administered, starting at day 17 of the celastrol treatment, at increasing doses (1 mg/kg, 2 mg/kg, and 4 mg/kg), as illustrated by the bar included above the x-axis of the graph.

As shown in FIG. 14, the body weight of celastrol treated mice decreased gradually and reached a plateau at approximately day 17. At this point, leptin (1 mg/kg/day, i.p.) was administered to both control and celastrol groups. As shown in FIG. 14, celastrol treated mice responded to leptin by a decrease in body weight, a response that was potentiated by increasing doses of leptin.

Example 8: Administration of Celastrol to Prevent Obesity

Figure 15:
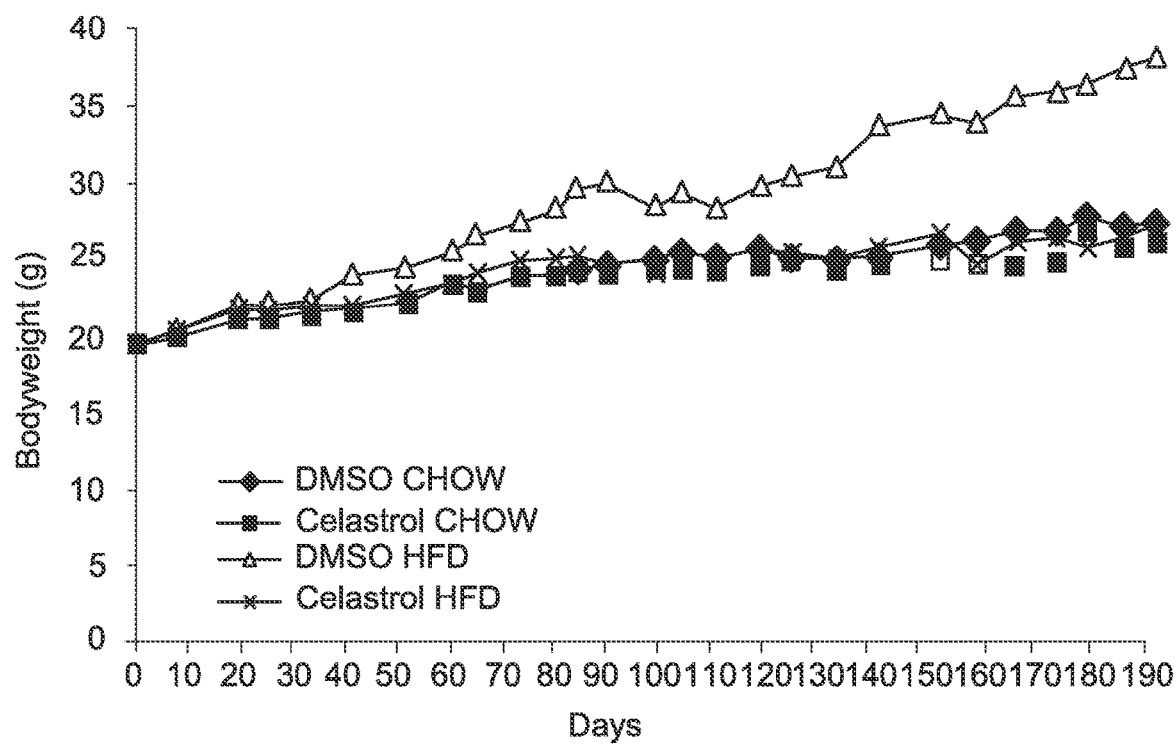
FIG. 15 is a graph plotting the average body weight (in grams) of four C57BL/6 mice (mice receiving regular chow diet and vehicle control (diamond trace), mice receiving regular chow diet and 100 μg/kg celastrol by i.p. once a day (square trace), HFD-fed mice receiving vehicle control (triangle trace), and HFD-fed mice receiving 100 μg/kg celastrol by i.p. once a day (cross trace)) as a function of time (days) for treatment. HFD-fed mice receiving the vehicle control developed obesity while the other groups of mice did not.

Four groups of C57BL/6 mice were taken at weaning at the age of 3 weeks. Two of the groups were put to regular chow diet, and two groups were put to high fat diet. One group from each diet received daily celastrol injections (100 μg/kg/day, i.p.), and the other group from each diet received vehicle injections (25 μL DMSO per day, i.p.) as a control for over 6 months. Bodyweights were measured throughout the study are reported in the attached figure. As shown FIG. 15, vehicle-HFD group developed obesity, while the other groups did not.

Figure 16A:
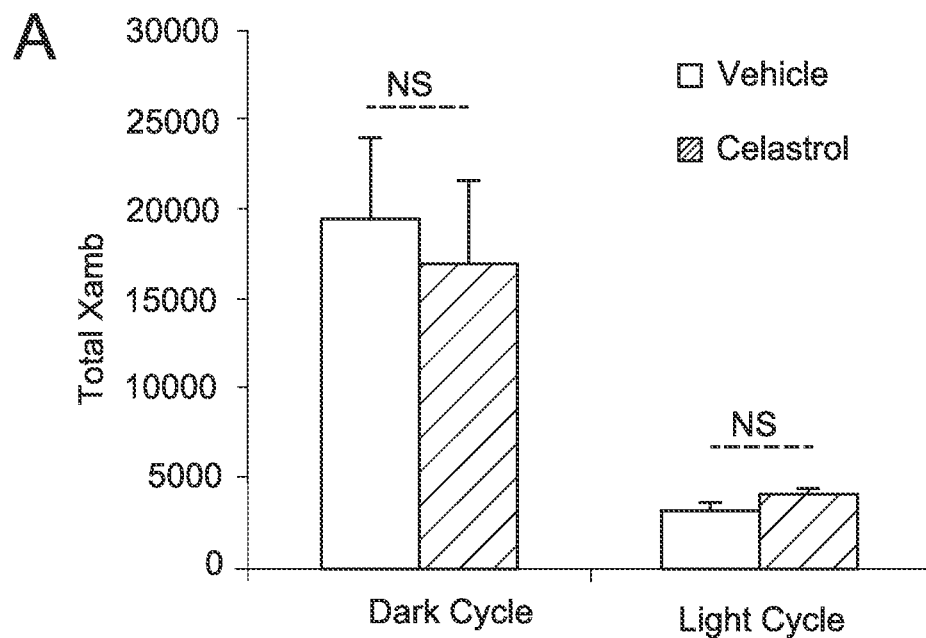
FIGS. 16A and 16B are graphs showing x (FIG. 16A) and y (FIG. 16B) direction ambulatory motion for control and celastrol in dark and light cycles. Toxicity was evaluated using Columbus Instruments Comprehensive Lab Animal Monitoring System. The locomotor activity of the animals was measured. As seen in the figures, x and y direction ambulatory motion counts of the animals during both the dark and light cycles are not significantly different. This shows that the drug treated mice are not lethargic and do not show any visible sign of sickness and toxicity.
Figure 16B:
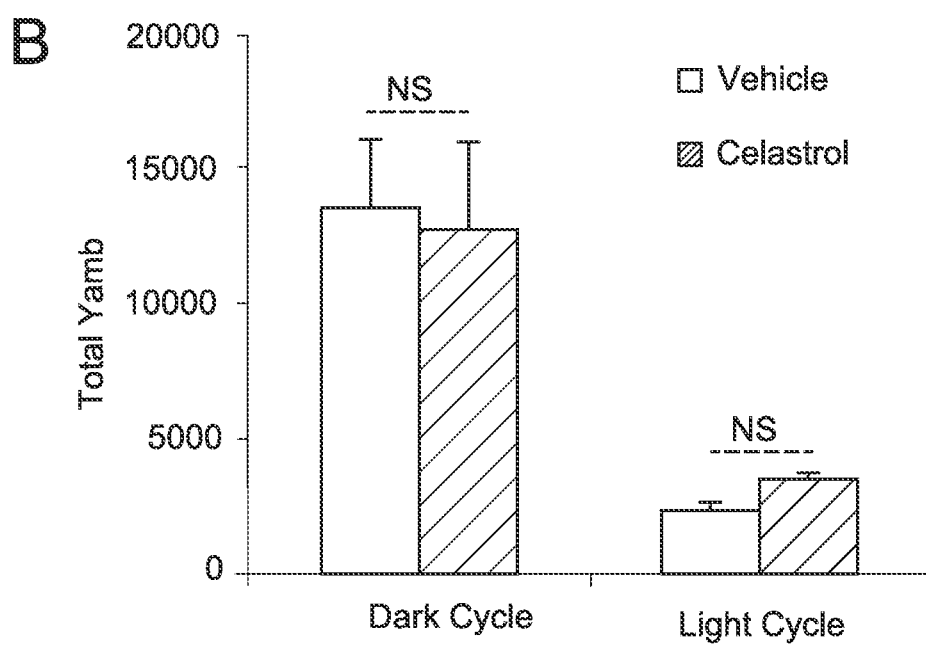

FIGS. 16A and 16B are graphs showing x (FIG. 16A) and y (FIG. 16B) direction ambulatory motion for control and celastrol in dark and light cycles. Toxicity was evaluated using Columbus Instruments Comprehensive Lab Animal Monitoring System we have measure the locomotor activity of the animals. As seen in the figures, x and y direction ambulatory motion counts of the animals during both the dark and light cycles are not significantly different. This shows that the drug treated mice are not lethargic so do not show any visible sign of sickness and toxicity.

We claim:

1. A pharmaceutical dosage formulation for oral administration of sustained or controlled release of an active agent to a pre-obese, obese, or morbidly obese human, the active agent consisting of celastrol

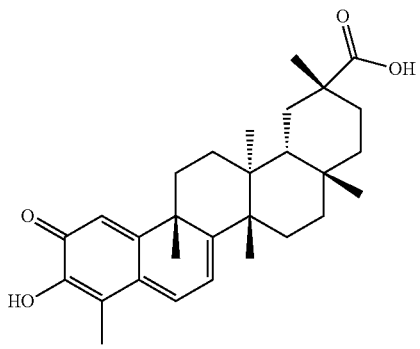

wherein the celastrol is present in an amount corresponding to a dosage of between 0.005 mg and 1 mg per kg of body weight of the human, which is effective to induce weight loss, reduce the body fat, reduce food intake, improve glucose homeostasis, or combinations thereof, in the pre-obese, obese, or morbidly obese human in the absence of systemic toxicity,
wherein the pharmaceutical dosage formulation is a powder or an oral suspension.

2. The pharmaceutical dosage formulation of claim 1, wherein the celastrol is present in an amount corresponding to a dosage of between 0.005 mg and 0.1 mg per kg of body weight of the human.

3. The pharmaceutical dosage formulation of claim 1, wherein the pharmaceutical dosage formulation is formulated for weekly administration.

4. A method of inducing weight loss, reducing the body fat, or combinations thereof, in a pre-obese, obese, or morbidly obese human, comprising orally administering to the human an effective amount of the pharmaceutical dosage formulation of claim 1.

5. The method of claim 4, wherein the effective amount is effective to reduce the average daily food calorie intake by at least 15% in the pre-obese, obese, or morbidly obese human.

6. The method of claim 4, wherein the effective amount is effective to decrease body fat in the pre-obese, obese, or morbidly obese human by at least 10%.

7. The method of claim 4, wherein the effective amount is effective to decrease body fat in the pre-obese, obese, or morbidly obese human by at least 20%.

8. The method of claim 4, wherein the effective amount is effective to decrease body mass in the pre-obese, obese, or morbidly obese human by at least 10%.

9. The method of claim 4, wherein the effective amount is effective to decrease body mass in the pre-obese, obese, or morbidly obese human by at least 20%.

10. The method of claim 4, wherein the effective amount is effective to reduce average fasting plasma blood glucose by at least 10%.

11. The method of claim 4, wherein the effective amount is effective to lower blood glucose levels to less than about 180 mg/dL.

12. The method of claim 4, wherein the pharmaceutical dosage formulation is administered in an amount corresponding to a dosage of celastrol of between 0.005 mg and 0.1 mg per kg of body weight of the human.

13. The method of claim 4, wherein the celastrol is administered weekly or less frequent.

14. The pharmaceutical dosage formulation of claim 1, wherein the pharmaceutical dosage formulation is formulated for administration twice a week or every two weeks.

15. The pharmaceutical dosage formulation of claim 14, wherein the pharmaceutical dosage formulation is formulated for administration every two weeks.

16. The pharmaceutical dosage formulation of claim 1, wherein the pharmaceutical dosage formulation is an oral suspension.

17. The pharmaceutical dosage formulation of claim 14, wherein the pharmaceutical dosage formulation is a powder.

18. The method of claim 4, wherein the pharmaceutical dosage formulation is administered twice a week or every two weeks.

19. The method of claim 4, wherein the pharmaceutical dosage formulation is administered every two weeks.

* * * * *